United States Patent
Barrett et al.

(10) Patent No.: US 6,750,217 B2
(45) Date of Patent: *Jun. 15, 2004

(54) BENZENESULFONAMIDE DERIVATIVES AND THEIR USE AS MEK INHIBITORS

(75) Inventors: Stephen Douglas Barrett, Livonia, MI (US); Haile Tecle, Ann Arbor, MI (US); Richard John Booth, Ann Arbor, MI (US)

(73) Assignee: Warner-Lambert Company, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 10/198,561

(22) Filed: Jul. 18, 2002

(65) Prior Publication Data

US 2003/0092748 A1 May 15, 2003

Related U.S. Application Data

(62) Division of application No. 09/869,639, filed as application No. PCT/US99/30435 on Dec. 21, 1999, now Pat. No. 6,440,966.
(60) Provisional application No. 60/115,874, filed on Jan. 13, 1999, and provisional application No. 60/122,422, filed on Mar. 2, 1999.

(51) Int. Cl.$^7$ .................. A61K 31/535; A61P 25/00
(52) U.S. Cl. .................. 514/237.8; 514/357; 514/603
(58) Field of Search ................ 514/237.8, 357, 514/603

(56) References Cited

U.S. PATENT DOCUMENTS 5,525,625 A  6/1996  Bridges et al. .......... 514/456
6,310,060 B1  10/2001  Barrett et al.

FOREIGN PATENT DOCUMENTS

WO  9837881  3/1998
WO  WO 99/01426  1/1999

OTHER PUBLICATIONS

PCT International Search Report, PCT/US99/30435.
A.N. Gaidukevich, et al., "Reactivity of Derivatives of Phenyl–Anthranilic Acid. IX. Acid–Base Properties of Sulfamoylic Derivatives of Phenyl–Anthranilic acid in mixed Solvent Dioxan–Water", Organic Reactivity, 1990, vol. 27, pp 152–158.

*Primary Examiner*—Deborah C. Lambkin
*Assistant Examiner*—Andrea D Small
(74) *Attorney, Agent, or Firm*—Peter C. Richardson; Garth Butterfield; Krishna G. Banerjee

(57) ABSTRACT

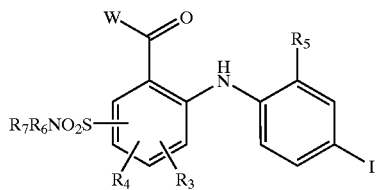

Benzenesulfonamides of formula (I), in which W is $OR_1$, $NR_2OR_1$, $NR_AR_B$, $NR_2NR_AR_B$, or $NR_2(CH_2)_{2-4}NR_AR_B$ and the other variables as defined in the claims, are inhibitors of MEK and are effective in the treatment of proliferative diseases, cancer, stroke, heart failure, xenograft rejection, arthritis, cystic fibrosis, hepatomegaly, cardiomegaly, Alzheimer's disease, complications of diabetes, septic shock, and viral infection.

3 Claims, No Drawings

BENZENESULFONAMIDE DERIVATIVES AND THEIR USE AS MEK INHIBITORS

This application is a Divisional application of U.S. Ser. No. 09/869,639 filed Jul. 2, 2001, issued as U.S. Pat. No. 6,440,966 on Aug. 27, 2002, which is a 371 application of PCT/US99/30435 filed Dec. 21, 1999, which claims the benefit of priority to U.S. provisional application Serial No. 60/115,874 filed Jan. 13, 1999 and U.S. provisional application Serial No. 60/122,422 filed Mar. 2, 1999.

The invention relates to benzenesulfonamides and derivatives thereof.

BACKGROUND

MEK enzymes are dual specificity kinases involved in, for example, immunomodulation, inflammation, and proliferative diseases such as cancer and restenosis.

Proliferative diseases are caused by a defect in the intracellular signaling system, or the signal transduction mechanism of certain proteins. Defects include a change either in the intrinsic activity or in the cellular concentration of one or more signaling proteins in the signaling cascade. The cell may produce a growth factor that binds to its own receptors, resulting in an autocrine loop, which continually stimulates proliferation. Mutations or overexpression of intracellular signaling proteins can lead to spurious mitogenic signals within the cell. Some of the most common mutations occur in genes encoding the protein known as Ras, a G-protein that is activated when bound to GTP, and inactivated when bound to GDP. The above-mentioned growth factor receptors, and many other mitogenic receptors, when activated, lead to Ras being converted from the GDP-bound state to the GTP-bound state. This signal is an absolute prerequisite for proliferation in most cell types. Defects in this signaling system, especially in the deactivation of the Ras-GTP complex, are common in cancers, and lead to the signaling cascade below Ras being chronically activated.

Activated Ras leads in turn to the activation of a cascade of serine/threonine kinases. One of the groups of kinases known to require an active Ras-GTP for its own activation is the Raf family. These in turn activate MEK (e.g., $MEK_1$ and $MEK_2$) which then activates MAP kinase, ERK ($ERK_1$ and $ERK_2$). Activation of MAP kinase by mitogens appears to be essential for proliferation; constitutive activation of this kinase is sufficient to induce cellular transformation. Blockade of downstream Ras signaling, for example by use of a dominant negative Raf-1 protein, can completely inhibit mitogenesis, whether induced from cell surface receptors or from oncogenic Ras mutants. Although Ras is not itself a protein kinase, it participates in the activation of Raf and other kinases, most likely through a phosphorylation mechanism. Once activated, Raf and other kinases phosphorylate MEK on two closely adjacent serine residues, $S^{218}$ and $S^{222}$ in the case of MEK-1, which are the prerequisite for activation of MEK as a kinase. MEK in turn phosphorylates MAP kinase on both a tyrosine, $Y^{185}$, and a threonine residue, $T^{183}$, separated by a single amino acid. This double phosphorylation activates MAP kinase at least 100-fold. Activated MAP kinase can then catalyze the phosphorylation of a large number of proteins, including several transcription factors and other kinases. Many of these MAP kinase phosphorylations are mitogenically activating for the target protein, such as a kinase, a transcription factor, or another cellular protein. In addition to Raf-1 and MEKK, other kinases activate MEK, and MEK itself appears to be a signal integrating kinase. Current understanding is that MEK is highly specific for the phosphorylation of MAP kinase. In fact, no substrate for MEK other than the MAP kinase, ERK, has been demonstrated to date and MEK does not phosphorylate peptides based on the MAP kinase phosphorylation sequence, or even phosphorylate denatured MAP kinase. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

SUMMARY

The invention features a compound having the formula (I) below:

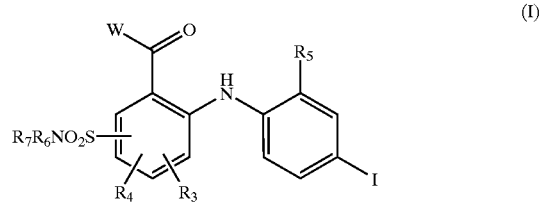

W is $OR_1$, $NR_2OR_1$, $NR_AR_B$, $NR_2NR_AR_B$, or $NR_2(CH_2)_{2-4}NR_AR_B$. $R_1$ is H, $C_{1-8}$ alkyl, $C_{3-8}$ alkenyl, $C_{3-8}$ alkynyl, $C_{3-8}$ cycloalkyl, phenyl, (phenyl)$C_{1-4}$ alkyl, (phenyl)$C_{3-4}$ alkenyl, (phenyl)$C_{3-4}$ alkynyl, ($C_{3-8}$ cycloalkyl)-$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, ($C_{3-8}$ heterocyclic radical)$C_{3-4}$ alkenyl, ($C_{3-8}$ heterocyclic radical)$C_{3-4}$ alkynyl, or $(CH_2)_{2-4}NR_AR_B$. $R_2$ is H, phenyl, $C_{1-4}$ alkyl, $C_{3-4}$ alkenyl $C_{3-8}$ alkynyl, $C_{3-8}$ cycloalkyl, or ($C_{3-8}$ cycloalkyl)$C_{1-4}$ alkyl. $R_A$ is H, $C_{1-6}$ alkyl, $C_{3-8}$ alkenyl, $C_{3-8}$ alkynyl, $C_{3-8}$ cycloalkyl, phenyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, (aminosulfonyl)phenyl, [(aminosulfonyl)phenyl]$C_{1-4}$ alkyl, (aminosulfonyl)$C_{1-6}$ alkyl, (aminosulfonyl)$C_{3-6}$ cycloalkyl, or [(aminosulfonyl)$C_{3-6}$ cycloalkyl]$C_{1-4}$ alkyl. $R_B$ is H, $C_{1-8}$ alkyl, $C_{3-8}$ alkenyl, $C_{3-8}$ alkynyl, $C_{3-8}$ cycloalkyl, or $C_{6-8}$ aryl. $R_3$ is H, F, Cl, Br, or $NO_2$. $R_4$ is H or F. $R_5$ is H, methyl or Cl. $R_6$ is H, $C_{1-4}$ alkyl, hydroxyethyl, hydroxypropyl, $(CH_2)_{2-4}(NR_CR_D)$, phenyl, 2-pyridyl, 3-pyridyl, 4-pyridyl or $CH_2Ar$, where Ar is phenyl, 2-pyridyl, 3-pyridyl, or 4-pyridyl. $R_7$ is H, $C_{1-4}$ alkyl, hydroxyethyl, hydroxypropyl, $(CH_2)_{2-4}(NR_CR_D)$, phenyl, 2-pyridyl, 3-pyridyl, 4-pyridyl, or $CH_2Ar'$, where Ar' is phenyl, 2-pyridyl, 3-pyridyl, or 4-pyridyl. Each of $R_C$ and $R_D$ is independently selected from H, $C_{1-6}$ alkyl, $C_{3-4}$ alkenyl, $C_{3-4}$ alkynyl, $C_{3-6}$ cycloalkyl, $C_{3-6}$ heterocyclic radical, and phenyl. $NR_CR_D$ can also be selected from morpholinyl, piperazinyl, pyrrolidinyl, or piperadinyl. Each hydrocarbon radical or heterocyclic radical above is optionally substituted with between 1 and 3 substituents independently selected from halo, $C_{1-4}$ alkyl, $C_{3-6}$ cycloalkyl, $C_{2-4}$ alkenyl, $C_{2-4}$ alkynyl, phenyl, hydroxy, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$ alkyl, hydroxy, amino, and $NO_2$. The invention also features pharmaceutically acceptable salts and $C_{1-7}$ esters thereof.

Preferred compounds include PD 297764, 3,4-Difluoro-2-(4-iodo-phenylamino)-N-methoxy-5-(4-pyridin-2-yl-piperazine-1-sulfonyl)-benzamide; PD 297765, N-Allyloxy-3,4-difluoro-2-(4-iodo-phenylamino)-5-(4-methyl-piperazine-1-sulfonyl)-benzamide; PD297766, N-Allyloxy-5-[(2-diethylamino-ethyl)-methyl-sulfamoyl]-3,4-difluoro-2-(4-iodo-phenylamino)-benzamide; PD297767, N-Allyloxy-5-[(3-dimethylamino-propyl)-methyl-sulfamoyl]-3,4-difluoro-2-(4-iodo-phenylamino)-benzamide; PD297768, N-Cyclopropylmethoxy-3,4-difluoro-2-(4-iodo-phenylamino)-5-(4-methyl-piperazine-1-sulfonyl)-benzamide; PD297769, N-Cyclopropylmethoxy-5-[(2-diethylamino-ethyl)-methyl-sulfamoyl]-3,4-difluoro-2-(4-iodo-phenylamino)-benzamide; PD297770, N-Cyclopropylmethoxy-3,4-difluoro-2-(4-iodo-phenylamino)-5-[methyl-(2-pyridin-2-yl-ethyl)-sulfamoyl]-benzamide; PD297771, N-Cyclopropylmethoxy-3,4-difluoro-2-(4-iodo-phenylamino)-5-(4-pyridin-2-yl-piperazine-1-sulfonyl)-benzamide; PD297772, 5-[Benzyl-(2-dimethylamino-ethyl)-sulfamoyl]-N-cyclopropyl-methoxy-3,4-difluoro-2-(4-iodo-phenylamino)-benzamide; PD297773, 3,4-Difluoro-2-(4-iodo-2-methyl-phenylamino)-N-methoxy-5-(4-pyridin-2-yl-piperazine-1-sulfonyl)-benzamide; and PD297774, 1-[5-Allyloxycarbamoyl-2,3-difluoro-4-(4-iodo-2-methyl-phenylamino)-benzenesulfonyl]-piperidine-3-carboxylic acid amide.

The invention also relates to a pharmaceutical composition including (a) a compound of formula (I) and (b) a pharmaceutically-acceptable carrier.

The invention further relates to a method for treating proliferative diseases, such as cancer, restenosis, psoriasis, autoimmune disease, and atherosclerosis. Other aspects of the invention include methods for treating MEK-related (including ras-related) cancers, whether solid or hematopoietic. Examples of cancers include colorectal, cervical, breast, ovarian, brain, acute leukemia, gastric, non-small cell lung, pancreatic and renal cancer. Further aspects of the invention include methods for treating or reducing the symptoms of xenograft (cell(s), skin, limb, organ or bone marrow transplant) rejection, osteoarthritis, rheumatoid arthritis, cystic fibrosis, complications of diabetes (including diabetic retinopathy and diabetic nephropathy), hepatomegaly, cardiomegaly, stroke (such as acute focal ischemic stroke and global cerebral ischemia), heart failure, septic shock, asthma, and Alzheimer's disease. Compounds of the invention are also useful as antiviral agents for treating viral infections such as HIV, hepatitis B virus (HBV), human papilloma virus (HPV), cytomegalovirus (CMV), and Epstein-Barr virus (EBV). These methods include the step of administering to a patient in need of such treatment, or suffering from such a disease or condition, a pharmaceutically-effective amount of a disclosed compound or pharmaceutical composition thereof.

The invention also features methods of combination therapy, such as a method for treating cancer, wherein the method further includes providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4 (1H, 3H)-pyrimidinedione (5FU), flutamide, and gemcitabine. The chemotherapy or radiation therapy may be administered before, concurrently, or after the administration of a disclosed compound according to the needs of the patient.

The invention also features synthetic methods and synthetic intermediates disclosed herein.

Other aspects of the invention are provided in the description, examples, and claims below.

DETAILED DESCRIPTION

The invention features benzenesulfonamide compounds, pharmaceutical compositions thereof, and methods of using such compounds and compositions.

According to one aspect of the invention, the compounds are MEK inhibitors. MEK inhibition assays include the cascade assay for inhibitors of MAP kinase pathway described at column 6, line 36 to column 7, line 4 of U.S. Pat. No. 5,525,625 and the in vitro MEK assay at column 7, lines 4–27 of the same patent, the entire disclosure of which is incorporated by reference (see also Examples 5–10 below).

A. Terms

Certain terms are defined below and by their usage throughout this disclosure.

Alkyl groups include aliphatic (i.e., hydrocarbyl or hydrocarbon radical structures containing hydrogen and carbon atoms) with a free valence. Alkyl groups are understood to include straight chain and branched structures. Examples include methyl, ethyl, propyl, isopropyl, butyl, n-butyl, isobutyl, t-butyl, pentyl, isopentyl, 2,3-dimethylpropyl, hexyl, 2,3-dimethylhexyl, 1,1-dimethylpentyl, heptyl, and octyl. Cycloalkyl groups include cyclopropyl, cyclobutyl, cyclopentyl, cyclohexyl, cycloheptyl, and cyclooctyl.

Alkyl groups can be substituted with 1, 2, 3 or more substituents which are independently selected from halo (fluoro, chloro, bromo, or iodo), hydroxy, amino, alkoxy, alkylamino, dialkylamino, cycloalkyl, aryl, aryloxy, arylalkyloxy, heterocyclic radical, and (heterocyclic radical) oxy. Specific examples include fluoromethyl, hydroxyethyl, 2,3-dihydroxyethyl, (2- or 3-furanyl)methyl, cyclopropylmethyl, benzyloxyethyl, (3-pyridinyl)methyl, (2- or 3-furanyl)methyl, (2-thienyl)ethyl, hydroxypropyl, aminocyclohexyl, 2-dimethylaminobutyl, methoxymethyl, N-pyridinylethyl, diethylaminoethyl, and cyclobutylmethyl.

Alkenyl groups are analogous to alkyl groups, but have at least one double bond (two adjacent $sp^2$ carbon atoms). Depending on the placement of a double bond and substituents, if any, the geometry of the double bond may be entgegen (E), or zusammen (Z), cis, or trans. Similarly, alkynyl groups have at least one triple bond (two adjacent sp carbon atoms). Unsaturated alkenyl or alkynyl groups may have one or more double or triple bonds, respectively, or a mixture thereof; like alkyl groups, unsaturated groups may be straight chain or branched, and they may be substituted as described both above for alkyl groups and throughout the disclosure by example. Examples of alkenyls, alkynyls, and substituted forms include cis-2-butenyl, trans-2-butenyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl, and 2-methyl-2-propenyl.

In formula (I), alkenyls and alkynyls can be $C_{2-4}$ or $C_{2-8}$, and are preferably $C_{3-4}$ or $C_{3-8}$.

More general forms of substituted hydrocarbon radicals include hydroxyalkyl, hydroxyalkenyl, hydroxyalkynyl, hydroxycycloalkyl, hydroxyaryl, and corresponding forms for the prefixes amino-, halo- (e.g., fluoro-, chloro-, or bromo-), nitro-, alkyl-, phenyl-, cycloalkyl- and so on, or combinations of substituents. According to formula (I), therefore, substituted alkyls include hydroxyalkyl, aminoalkyl, nitroalkyl, haloalkyl, alkylalkyl (branched alkyls, such as methylpentyl), (cycloalkyl)alkyl, phenylalkyl, alkoxy, alkylaminoalkyl, dialkylaminoalkyl, arylalkyl, aryloxyalkyl, arylalkyloxyalkyl, (heterocyclic radical)alkyl, and (heterocyclic radical)oxyalkyl. $R_1$ thus includes hydroxyalkyl, hydroxyalkenyl, hydroxyalkynyl, hydroxycycloalkyl, hydroxyaryl, aminoalkyl, aminoalkenyl, aminoalkynyl, aminocycloalkyl, aminoaryl, alkylalkenyl, (alkylaryl)alkyl, (haloaryl)alkyl, (hydroxyaryl)alkynyl, and so forth. Similarly, $R_A$ includes hydroxyalkyl and aminoaryl, and $R_8$ includes hydroxyalkyl, aminoalkyl, and hydroxyalkyl(heterocyclic radical)alkyl.

Heterocyclic radicals, which include but are not limited to heteroaryls, include: furyl, oxazolyl, isoxazolyl, thiophenyl, thiazolyl, pyrrolyl, imidazolyl, 1,3,4-triazolyl, tetrazolyl, pyridinyl, pyrimidinyl, pyridazinyl, indolyl, and their non-aromatic counterparts. Further examples of heterocyclic radicals include piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl.

Selective MEK 1 or MEK 2 inhibitors are those compounds which inhibit the MEK 1 or MEK 2 enzymes, respectively, without substantially inhibiting other enzymes such as MKK3, PKC, Cdk2A, phosphorylase kinase, EGF, and PDGF receptor kinases, and C-src. In general, a selective MEK 1 or MEK 2 inhibitor has an $IC_{50}$ for MEK 1 or MEK 2 that is at least one-fiftieth (1/50) that of its $IC_{50}$ for one of the above-named other enzymes. Preferably, a selective inhibitor has an $IC_{50}$ that is at least 1/100, more preferably 1/500, and even more preferably 1/1000, 1/5000, or less than that of its $IC_{50}$ or one or more of the above-named enzymes.

B. Compounds

One aspect of the invention features disclosed compounds shown in formula (I) in the Summary section.

Examples of compounds of formula (I) have structures wherein: (a) the sulfamoyl group is meta to W(CO)— and para to the bridging NH; (b) the sulfamoyl group is para to W(CO)— and meta to the bridging NH; (c) $R_4$ is fluoro; (d) $R_3$ is fluoro; (e) $R_3$ is H; (f) W is OH; (g) W is $NR_2OR_1$; (h) each of $R_3$ and $R_4$ is fluoro; (i) $R_1$ has at least one hydroxy substituent; (k) $R_1$ is H, methyl, ethyl, propyl, isopropyl, isobutyl, benzyl, phenethyl, allyl, $C_{2-5}$ alkenyl, $C_{2-5}$ alkynyl, $C_{3-6}$ cycloalkyl, ($C_{3-5}$ cycloalkyl)$C_{1-2}$ alkyl, ($C_{3-5}$ heterocyclic radical)-$C_{1-2}$ alkyl, or $(CH_2)_{2-4}NR_AR_B$; (l) $R_1$ is H or ($C_{3-4}$ cycloalkyl)$C_{1-2}$ alkyl; (m) $R_2$ is H, methyl, $C_{2-4}$ alkynyl, $C_{3-5}$ cycloalkyl, or ($C_{3-5}$ cycloalkyl)methyl; (n) $R_A$ is H, methyl, ethyl, isobutyl, hydroxyethyl, hydroxypropyl, cyclopropylmethyl, cyclobutylmethyl, $C_{3-4}$ alkynyl, phenyl, 2-piperidin-1-yl-ethyl, 2,3-dihydroxy-propyl, 3-[4-(2-hydroxyethyl)-piperazin-1-yl]-propyl, 2-pyrrolidin-1-yl-ethyl, or 2-diethylamino-ethyl; and $R_B$ is H; or where $R_B$ is methyl and $R_A$ is phenyl; (O)$R_7$ is $(CH_2)_{2-4}(NR_CR_D)$; (p) $NR_CRD$ is selected from morpholinyl, piperazinyl, pyrrolidinyl, or piperadinyl; (q) $R_C$ is methyl, ethyl, hydroxyethyl, or hydroxypropyl; (r) $R_5$ is methyl or chloro; (s) $R_D$ is methyl, ethyl, hydroxyethyl, or hydroxypropyl; (t) or combinations thereof, such as wherein each of $R_C$ and $R_D$ is methyl or ethyl.

Preferably, where one of $R_1$, $R_2$, $R_A$, $R_B$, $R_C$, or $R_D$ is an alkenyl or alkynyl group, the double or triple bond, respectively, is not adjacent the point of attachment. For example, where W is $NR_2OR_1$, $R_2$ is preferably prop-2-ynyl, or but-2 or 3-enyl, and less preferably prop-1-ynyl or but-1-enyl.

Examples of compounds of formula (I) include: 2-(2-chloro-4-iodo-phenylamino)-4-sulfamoyl-benzoic acid; 2-(2-chloro-4-iodo-phenylamino)-N-hydroxy-4-sulfamoyl-benzamide; 2-(2-chloro-4-iodo-phenylamino)-N-cyclopropylmethoxy-4-sulfamoyl-benzamide; 2-(2-chloro-4-iodo-phenylamino)-4-(2-morpholin-4-yl-ethylsulfamoyl)-benzoic acid; 2-(2-chloro-4-iodo-phenylamino)-N-hydroxy-4-(2-morpholin-4-yl-ethylsulfamoyl)-benzamide; 2-(2-chloro-4-iodo-phenylamino)-N-cyclopropylmethoxy-4-(2-morpholin-4-yl-ethylsulfamoyl)-benzamide; 2-(2-chloro-4-iodo-phenylamino)-3,4-difluoro-5-sulfamoyl-benzoic acid; 2-(2-chloro-4-iodo-phenylamino)-3,4-difluoro-N-hydroxy-5-sulfamoyl-benzamide; 2-(2-chloro-4-iodo-phenylamino)-N-cyclopropylmethoxy-3,4-difluoro-5-sulfamoyl-benzamide; 2-(2-chloro-4-iodo-phenylamino)-3,4-difluoro-5-(2-morpholin-4-yl-ethylsulfamoyl)-benzoic acid; 2-(2-chloro-4-iodo-phenylamino)-3,4-difluoro-N-hydroxy-5-(2-morpholin-4-yl-ethylsulfamoyl)-benzamide; and 2-(2-chloro-4-iodo-phenylamino)-N-cyclopropylmethoxy-3,4-difluoro-5-(2-morpholin-4-yl-ethylsulfamoyl)-benzamide.

Other examples include 5-[bis-(4-methoxy-benzyl)-sulfamoyl]-2-(2-chloro-4-iodo-phenylamino)-3,4-difluoro-benzoic acid; and 2-(2-chloro-4-iodo-phenylamino)-5-dimethylsulfamoyl-3,4-difluoro-benzoic acid methyl ester.

Additional examples include 5-(bis-pyridin-3-ylmethyl-sulfamoyl)-3,4-difluoro-2-(4-iodo-phenylamino)-benzoic acid; 5-(bis-pyridin-3-ylmethyl-sulfamoyl)-N-cyclopropylmethoxy-3,4-difluoro-2-(4-iodo-phenylamino)-benzamide; N-cyclopropylmethoxy-3,4-difluoro-2-(4-iodo-phenylamino)-5-(methyl-pyridin-3-ylmethyl-sulfamoyl)-benzamide; N-cyclopropylmethoxy-3,4-difluro-2-4-iodo-phenylamino)-5-[(pyridin-3-ylmethyl)-sulfamoyl]-benzamide; N-cyclopropylmethoxy-5-[(3-diethylamino-propyl)-pyridin-3-ylmethyl-sulfamoyl]-3,4-difluoro-2-(4-iodo-phenylamino)-benzamide; N-cyclopropylmethoxy-3, 4-difluoro-5-[(3-hydroxy-propyl)-pyridin-3-ylmethyl-sulfamoyl]-2-(4-iodo-phenylamino)-benzamide; N-cyclopropylmethoxy-5-(ethyl-pyridin-3-ylmethyl-sulfamoyl)-3,4-difluoro-2-(4-iodo-phenylamino)-benzamide; N-cyclopropylmethoxy-3,4-difluoro-5-[(2-hydroxy-ethyl)-pyridin-3-ylmethyl-sulfamoyl]-2-(4-iodo-phenylamino)-benzamide; 5-(bis-pyridin-2-ylmethyl-sulfamoyl)-3,4-difluoro-2-(4-iodo-phenylamino)-benzoic acid; 5-(bis-pyridin-2-ylmethyl-sulfamoyl)-N-cyclopropylmethoxy-3,4-difluoro-2-(4-iodo-phenylamino)-benzamide; N-cyclopropylmethoxy-3,4-difluoro-2-(4-iodo-phenylamino)-5-(methyl-pyridin-2-ylmethyl-sulfamoyl)-benzamide; N-cyclopropylmethoxy-3,4-difluoro-2-(4-iodo-phenylamino)-5-[(pyridin-2-ylmethyl)-sulfamoyl]-benzamide; 5-(bis-pyridin-3-ylmethyl-sulfamoyl)-3,4-difluoro-2-(4-iodo-2-methyl-phenylamino)-benzoic acid; 5-(bis-pyridin-3-ylmethyl-sulfamoyl)-N-cyclopropylmethoxy-3,4-difluoro-2-(4-iodo-2-methyl-phenylamino)-benzamide; N-cyclopropylmethoxy-3,4-difluoro-2-(4-iodo-2-methyl-phenylamino)-5-(methyl-pyridin-3-ylmethyl-sulfamoyl)-benzamide; N-cyclopropylmethoxy-3,4-difluoro-2-(4-iodo-2-methyl-phenylamino)-5-[(pyridin-3-ylmethyl)-sulfamoyl]-benzamide; N-cyclopropylmethoxy-5-[(3-diethylamino-propyl)-pyridin-3-ylmethyl-sulfamoyl]-3,4-difluoro-2-(4-iodo-2-methyl-phenylamino)-benzamide; N-cyclopropylmethoxy-3,4-difluoro-5-[(3-hydroxy-propyl)-pyridin-3-ylmethyl-sulfamoyl]-2-(4-iodo-2-methyl-phenylamino)-benzamide; N-cyclopropylmethoxy-5-(ethyl-pyridin-3-ylmethyl-sulfamoyl)-3,4-difluoro-2-(4-iodo-2-methyl-phenylamino)-benzamide; N-cyclopropylmethoxy-3,4-difluoro-5-[(2-hydroxy-ethyl)-pyridin-3-ylmethyl-sulfamoyl]-2-(4-iodo-2-methyl-phenylamino)-benzamide; 5-(bis-pyridin-2-ylmethyl-sulfamoyl)-3,4-difluoro-2-(4- iodo-2-methyl-phenylamino)-benzoic acid; 5-(bis-pyridin-2-ylmethyl-sulfamoyl)-N-cyclopropylmethoxy-3,4-difluoro-2-(4-iodo-2-methyl-phenylamino)-benzamide; N-cyclopropylmethoxy-3,4-difluoro-2-(4-iodo-2-methyl-phenylamino)-5-(methyl-pyridin-2-ylmethyl-sulfamoyl)-benzamide; N-cyclopropylmethoxy-3,4-difluoro-2-(4-iodo-2-methyl-phenylamino)-5-[(pyridin-2-ylmethyl)-sulfamoyl]-benzamide; 5-(bis-pyridin-3-ylmethyl-sulfamoyl)-2-(2-chloro-4-iodo-phenylamino)-3,4-difluoro-benzoic acid, 5-(bis-pyridin-3-ylmethyl-sulfamoyl)-2-(2-chloro-4-iodo-phenylamino)-N-cyclopropylmethoxy-3,4-difluoro-benzamide; 2-(2-chloro-4-iodo-phenylamino)-N-cyclopropylmethoxy-3,4-difluoro-5-(methyl-pyridin-3-ylmethyl-sulfamoyl)-benzamide; 2-(2-chloro-4-iodo-phenylamino)-N-cyclopropylmethoxy-3,4-difluoro-5-[(pyridin-3-ylmethyl)-sulfamoyl]-benzamide; 2-(2-chloro-4-iodo-phenylamino)-N-cyclopropylmethoxy-5-[(3-diethylamino-propyl)-pyridin-3-ylmethyl-sulfamoyl]-3,4-difluoro-benzamide; 2-(2-chloro-4-iodo-phenylamino)-N-cyclopropylmethoxy-3,4-difluoro-5-[(3-hydroxy-propyl)-pyridin-3-ylmethyl-sulfamoyl]-benzamide; 2-(2-chloro-4-iodo-phenylamino)-N-cyclopropylmethoxy-5-(ethyl-pyridin-3-ylmethyl-sulfamoyl)-3,4-difluoro-benzamide; 2-(2-chloro-4-iodo-phenylamino)-N-cyclopropylmethoxy-3,4-difluoro-5-[(2-hydroxy-ethyl)-pyridin-3-ylmethyl-sulfamoyl]-benzamide; 5-(bis-pyridin-2-ylmethyl-sulfamoyl)-2-(2-chloro-4-iodo-phenylamino)-3,4-difluoro-benzoic acid; 5-(bis-pyridin-2-ylmethyl-sulfamoyl)-2-(2-chloro-4-iodo-phenylamino)-N-cyclopropylmethoxy-3,4-difluoro-benzamide; 2-(2-chloro-4-iodo-phenylamino)-N-cyclopropylmethoxy-3,4-difluoro-5-(methyl-pyridin-2-ylmethyl-sulfamoyl)-benzamide; 2-(2-chloro-4-iodo-phenylamino)-N-cyclopropylmethoxy-3,4-difluoro-5-[(pyridin-2-ylmethyl)-sulfamoyl]-benzamide; N-cyclopropylmethoxy-3,4-difluoro-5-[(3-hydroxy-propyl)-pyridin-2-ylmethyl-sulfamoyl]-2-(4-iodo-phenylamino)-benzamide; N-cyclopropylmethoxy-3,4-difluoro-5-[(2-hydroxy-ethyl)-pyridin-2-ylmethyl-sulfamoyl]-2-(4-iodo-phenylamino)-benzamide; 5-(benzyl-pyridin-2-ylmethyl-sulfamoyl)-N-cyclopropylmethoxy-3,4-difluoro-2-(4-iodo-phenylamino)-benzamide; N-cyclopropylmethoxy-3,4-difluoro-2-(4-iodo-phenylamino)-5-[(pyridin-4-ylmethyl)-sulfamoyl]-benzamide; N-cyclopropylmethoxy-5-(ethyl-pyridin-4-ylmethyl-sulfamoyl)-3,4-difluoro-2-(4-iodo-phenylamino)-benzamide; N-cyclopropylmethoxy-3,4-difluoro-2-(4-iodo-phenylamino)-5-(methyl-pyridin-4-ylmethyl-sulfamoyl)-benzamide; N-cyclopropylmethoxy-3,4-difluoro-5-[(3-hydroxy-propyl)-pyridin-4-ylmethyl-sulfamoyl]-2-(4-iodo-phenylamino)-benzamide; N-cyclopropylmethoxy-3,4-difluoro-5-[(2-hydroxy-ethyl)-pyridin-4-ylmethyl-sulfamoyl]-2-(4-iodo-phenylamino)-benzamide; N-cyclopropylmethoxy-3,4-difluoro-2-(4-iodo-phenylamino)-5-(methyl-phenyl-sulfamoyl)-benzamide; N-cyclopropylmethoxy-3,4-difluoro-2-(4-iodo-phenylamino)-5-phenylsulfamoyl-benzamide; N-Cyclopropylmethoxy-3,4-difluoro-2-(4-iodo-phenylamino)-5-(pyridin-3-ylsulfamoyl)-benzamide; N-cyclopropylmethoxy-3,4-difluoro-5-[(3-hydroxy-propyl)-pyridin-2-ylmethyl-sulfamoyl]-2-(4-iodo-2-methyl-phenylamino)-benzamide; N-cyclopropylmethoxy-3,4-difluoro-5-[(2-hydroxy-ethyl)-pyridin-2-ylmethyl-sulfamoyl]-2-(4-iodo-2-methyl-phenylamino)-benzamide; 5-(benzyl-pyridin-2-ylmethyl-sulfamoyl)-N-cyclopropylmethoxy-3,4-difluoro-2-(4-iodo-2-methyl-phenylamino)-benzamide; N-cyclopropylmethoxy-3,4-difluoro-2-(4-iodo-2-methyl-phenylamino)-5-[(pyridin-4-ylmethyl)-sulfamoyl]-benzamide; N-cyclopropylmethoxy-5-(ethyl-pyridin-4-yl methyl-sulfamoyl)-3,4-difluoro-2-(4-iodo-2-methyl-phenylamino)-benzamide; N-cyclopropylmethoxy-3,4-difluoro-2-(4-iodo-2-methyl-phenylamino)-5-(methyl-pyridin-4-ylmethyl-sulfamoyl)-benzamide; N-cyclopropylmethoxy-3,4-difluoro-5-[(3-hydroxy-propyl)-pyridin-4-ylmethyl-sulfamoyl]-2-(4-iodo-2-methyl-phenylamino)-benzamide; N-cyclopropylmethoxy-3,4-difluoro-5-[(2-hydroxy-ethyl)-pyridin-4-ylmethyl-sulfamoyl]-2-(4-iodo-2-methyl-phenylamino)-benzamide; N-cyclopropylmethoxy-3,4-difluoro-2-(4-iodo-2-methyl-phenylamino)-5-(methyl-phenyl-sulfamoyl)-benzamide; N-cyclopropylmethoxy-3,4-difluoro-2-(4-iodo-2-methyl-phenylamino)-5-phenylsulfamoyl-benzamide; N-cyclopropylmethoxy-3,4-difluoro-2-(4-iodo-2-methyl-phenylamino)-5-(pyridin-3-ylsulfamoyl)-benzamide; 2-(2-chloro-4-iodo-phenylamino)-N-cyclopropylmethoxy-3,4-difluoro-5-[(3-hydroxy-propyl)-pyridin-2-ylmethyl-sulfamoyl]-benzamide; 2-(2-chloro-4-iodo-phenylamino)-N-cyclopropylmethoxy-3,4-difluoro-5-[(2-hydroxy-ethyl)-pyridin-2-ylmethyl-sulfamoyl]-benzamide; 5-(benzyl-pyridin-2-ylmethyl-sulfamoyl)-2-(2-chloro-4-iodo-phenylamino)-N-cyclopropylmethoxy-3,4-difluoro-benzamide; 2-(2-chloro-4-iodo-phenylamino)-N-cyclopropylmethoxy-3,4-difluoro-5-[(pyridin-4-ylmethyl)-sulfamoyl]-benzamide; 2-(2-chloro-4-iodo-phenylamino)-N-cyclopropylmethoxy-5-(ethyl-pyridin-4-ylmethyl-sulfamoyl)-3,4-difluoro-benzamide; 2-(2-chloro-4-iodo-phenylamino)-N-cyclopropylmethoxy-3,4-difluoro-5-(methyl-pyridin-4-ylmethyl-sulfamoyl)-benzamide; 2-(2-chloro-4-iodo-phenylamino)-N-cyclopropylmethoxy-3,4-difluoro-5-[(3-hydroxy-propyl)-pyridin-4-ylmethyl-sulfamoyl]-benzamide; 2-(2-chloro-4-iodo-phenylamino)-N-cyclopropylmethoxy-3,4-difluoro-5-[(2-hydroxy-ethyl)-pyridin-4-ylmethyl-sulfamoyl]-benzamide; 2-(2-chloro-4-iodo-phenylamino)-N-cyclopropylmethoxy-3,4-difluoro-5-(methyl-phenyl-sulfamoyl)-benzamide; 2-(2-chloro-4-iodo-phenylamino)-N-cyclopropylmethoxy-3,4-difluoro-5-phenylsulfamoyl-benzamide; 2-(2-chloro-4-iodo-phenylamino)-N-cyclopropylmethoxy-3,4-difluoro-5-(pyridin-3-ylsulfamoyl)-benzamide; N-cyclopropyl-methoxy-2-(4-iodo-phenylamino)-4-phenylsulfamoyl-benzamide; N-cyclopropylmethoxy-2-(4-iodo-phenylamino)-4-(pyridin-3-ylsulfamoyl)-benzamide; N-cyclopropylmethoxy-2-(4-iodo-phenylamino)-4-[(pyridin-3-ylmethyl)-sulfamoyl]-benzamide; 4-(bis-pyridin-3-ylmethyl-sulfamoyl)-N-cyclopropylmethoxy-2-(4-iodo-phenylamino)-benzamide; N-cyclopropylmethoxy-4-[(2-hydroxy-ethyl)-pyridin-4-ylmethyl-sulfamoyl]-2-(4-iodo-phenylamino)-benzamide; N-cyclopropylmethoxy-2-(4-iodo-phenylamino)-4-(methyl-pyridin-3-ylmethyl-sulfamoyl)-benzamide; N-cyclopropylmethoxy-4-[(3-diethylamino-propyl)-pyridin-3-ylmethyl-sulfamoyl]-2-(4-iodo-phenylamino)-benzamide; N-cyclopropylmethoxy-2-(4-iodo-2-methyl-phenylamino)-4-phenylsulfamoyl-benzamide; N-cyclopropylmethoxy-2-(4-iodo-2-methyl-phenylamino)-4-(pyridin-3-ylsulfamoyl)-benzamide; N-cyclopropylmethoxy-2-(4-iodo-2-methyl-phenylamino)-4-[(pyridin-3-ylmethyl)-sulfamoyl]-benzamide; 4-(bis-pyridin-3-ylmethyl-sulfamoyl)-N-cyclopropylmethoxy-2-(4-iodo-2-methyl-phenylamino)-benzamide; N-cyclopropylmethoxy-4-[(2-hydroxy-ethyl)-pyridin-4-ylmethyl-sulfamoyl]-2-(4-iodo-2-methyl-phenylamino)-benzamide; N-cyclopropylmethoxy-2-(4-iodo-2-methyl-phenylamino)-4-(methyl-pyridin-3-ylmethyl-sulfamoyl)-benzamide; N-cyclopropylmethoxy-4-[(3-diethylaminopropyl)-pyridin-3-ylmethyl-sulfamoyl]-2-(4-iodo-2-methyl-phenylamino)-benzamide; 2-(2-chloro-4-iodo-phenylamino)-N-cyclopropylmethoxy-4-phenylsulfamoyl-benzamide; 2-(2-chloro-4-iodo-phenylamino)-N-cyclopropylmethoxy-4-(pyridin-3-ylsulfamoyl)-benzamide; 2-(2-chloro-4-iodo-phenylamino)-N-cyclopropylmethoxy-4-[(pyridin-3-ylmethyl)-sulfamoyl]-benzamide; 4-(bis-pyridin-3-ylmethyl-sulfamoyl)-2-(2-chloro-4-iodo-phenylamino)-N-cyclopropylmethoxy-benzamide; 2-(2-chloro-4-iodo-phenylamino)-N-cyclopropylmethoxy-4-[(2-hydroxy-ethyl)-pyridin-4-ylmethyl-sulfamoyl]-benzamide; 2-(2-chloro-4-iodo-phenylamino)-N-cyclopropylmethoxy-4-(methyl-pyridin-3-ylmethyl-sulfamoyl)-benzamide; and 2-(2-chloro-4-iodo-phenylamino)-N-cyclopropylmethoxy-4-[(3-diethylamino-propyl)-pyridin-3-ylmethyl-sulfamoyl]-benzamide.

Further examples include: PD 298469, 2-(2-Chloro-4-iodo-phenylamino)-3,4-difluoro-N-methoxy-5-(4-methyl-piperazine-1-sulfonyl)-benzamide; PD 298470, 2-(2-Chloro-4-iodo-phenylamino)-5-[(2-diethylamino-ethyl)-methyl-sulfamoyl]-3,4-difluoro-N-methoxy-benzamide; PD 298450, 2-(2-Chloro-4-iodo-phenylamino)-3,4-difluoro-N-methoxy-5-(methyl-prop-2-ynyl-sulfamoyl)-benzamide; PD 298451, 1-[4-(2-Chloro-4-iodo-phenylamino)-2,3-difluoro-5-methoxycarbamoyl-benzenesulfonyl]-piperidine-3-carboxylic acid amide;

PD 298452, 2-(2-Chloro-4-iodo-phenylamino)-3,4-difluoro-N-methoxy-5-[methyl-(2-pyridin-2-yl-ethyl)-sulfamoyl]-benzamide; PD 298453, 2-(2-Chloro-4-iodo-phenylamino)-5-[(3-dimethylamino-propyl)-methyl-sulfamoyl]-3,4-difluoro-N-methoxy-benzamide; PD 298454, 2-(2-Chloro-4-iodo-phenylamino)-3,4-difluoro-N-methoxy-5-(4-pyridin-2-yl-piperazine-1-sulfonyl)-benzamide; PD 298455, 5-[Bis-(2-methoxy-ethyl)-sulfamoyl]-2-(2-chloro-4-iodo-phenylamino)-3,4-difluoro-N-methoxy-benzamide; PD 298456, 5-[Benzyl-(2-dimethylamino-ethyl)-sulfamoyl]-2-(2-chloro-4-iodo-phenylamino)-3,4-difluoro-N-methoxy-benzamide; and PD 298457, N-Allyloxy-2-(2-chloro-4-iodo-phenylamino)-5-dimethylsulfamoyl-3,4-difluoro-benzamide; PD 298461, N-Allyloxy-2-(2-chloro-4-iodo-phenylamino)-3,4-difluoro-5-(methyl-prop-2-ynyl-sulfamoyl)-benzamide; PD 298462, N-Allyloxy-2-(2-chloro-4-iodo-phenylamino)-3,4-difluoro-5-[4-(4-fluoro-phenyl)-piperazine-1-sulfonyl]-benzamide; PD 298466, N-Allyloxy-5-[benzyl-(2-dimethylamino-ethyl)-sulfamoyl]-2-(2-chloro-4-iodo-phenylamino)-3,4-difluoro-benzamide; PD 298468, 2-(2-Chloro-4-iodo-phenylamino)-N-cyclopropylmethoxy-3,4-difluoro-5-(4-methyl-piperazine-1-sulfonyl)-benzamide; and PD 298449, 2-(2-Chloro-4-iodo-phenylamino)-3,4-difluoro-5-(methoxy-methyl-sulfamoyl)-N-(2-morpholin-4-yl-ethoxy)-benzamide.

Particularly preferred compounds include: PD 298458, N-Allyloxy-2-(2-chloro-4-iodo-phenylamino)-3,4-difluoro-5-(4-methyl-piperazine-1-sulfonyl)-benzamide; PD 298459, N-Allyloxy-2-(2-chloro-4-iodo-phenylamino)-3,4-difluoro-5-(methyl-phenyl-sulfamoyl)-benzamide; PD 298460, 5-(Allyl-methyl-sulfamoyl)-N-allyloxy-2-(2-chloro-4-iodo-phenylamino)-3,4-difluoro-benzamide; PD 298463, 1-[5-Allyloxycarbamoyl-4-(2-chloro-4-iodo-phenylamino)-2,3-difluoro-benzenesulfonyl]-piperidine-3-carboxylic acid amide; PD 298464, N-Allyloxy-2-(2-chloro-4-iodo-phenylamino)-5-[(3-dimethylamino-propyl)-methyl-sulfamoyl]-3,4-difluoro-benzamide; PD 298465, N-Allyloxy-2-(2-chloro-4-iodo-phenylamino)-3,4-difluoro-5-(4-pyridin-2-yl-piperazine-1-sulfonyl)-benzamide; and PD 298467, N-Allyloxy-2-(2-chloro-4-iodo-phenylamino)-3,4-difluoro-5-(methoxy-methyl-sulfamoyl)-benzamide.

C. Synthesis

The disclosed compounds can be synthesized according to the following four Schemes, or variants thereof. These synthetic strategies, which are suitable for conventional or combinatorial synthetic methods, are further exemplified in Examples 1–4 below.

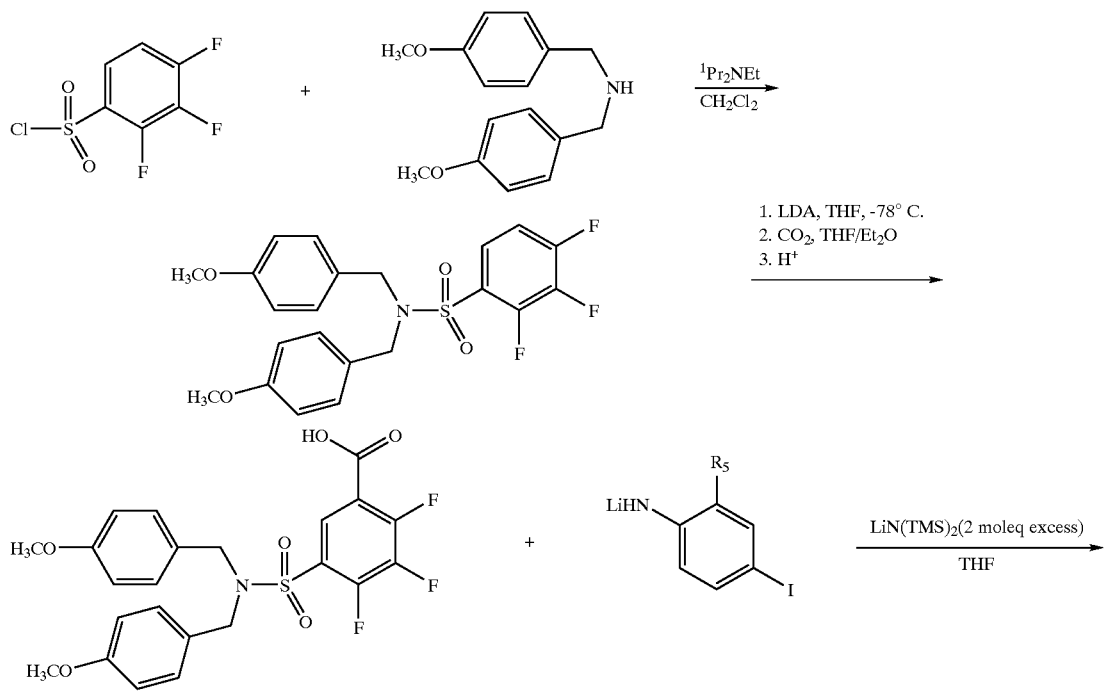

Scheme 1

-continued
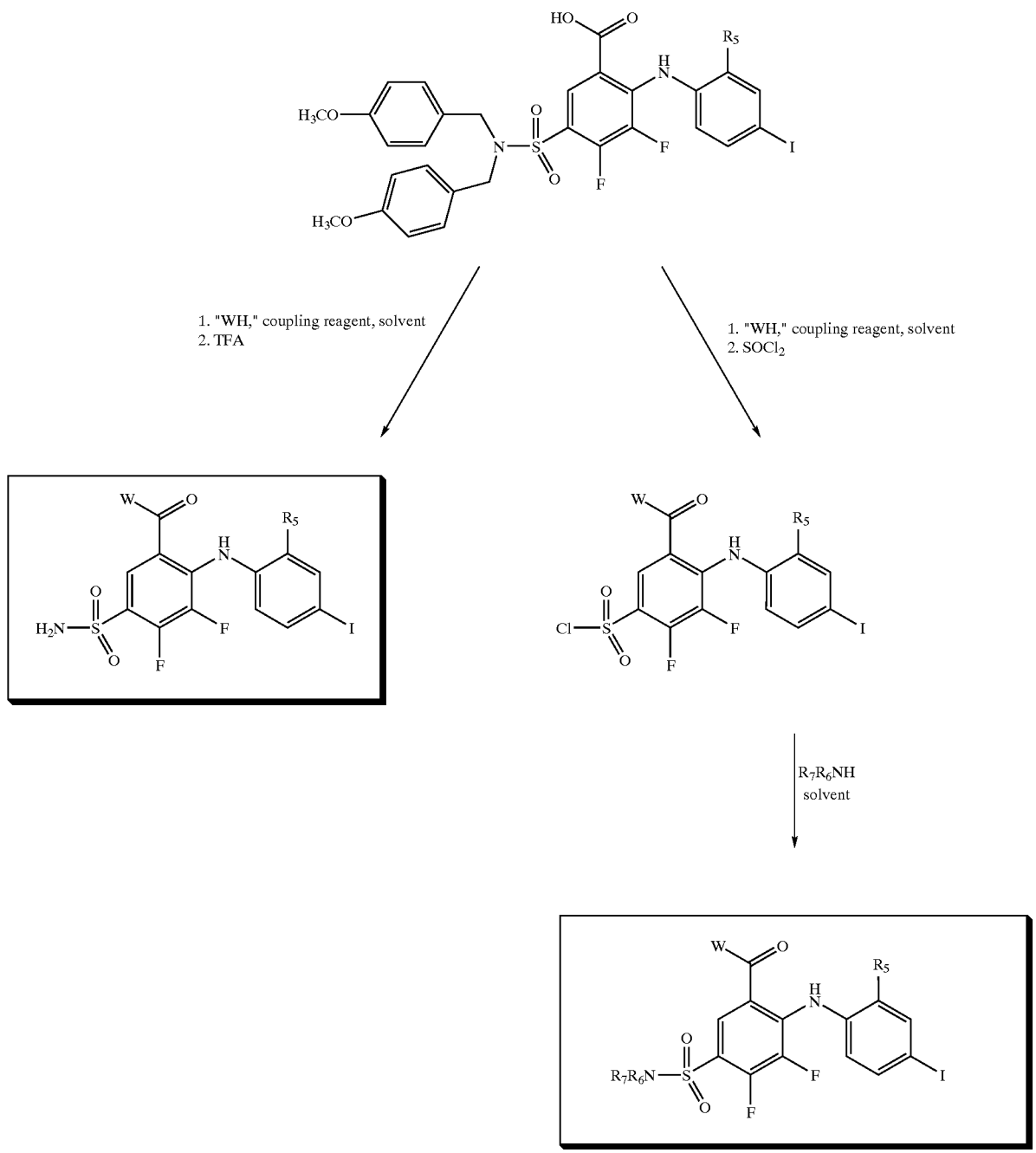
Scheme 2
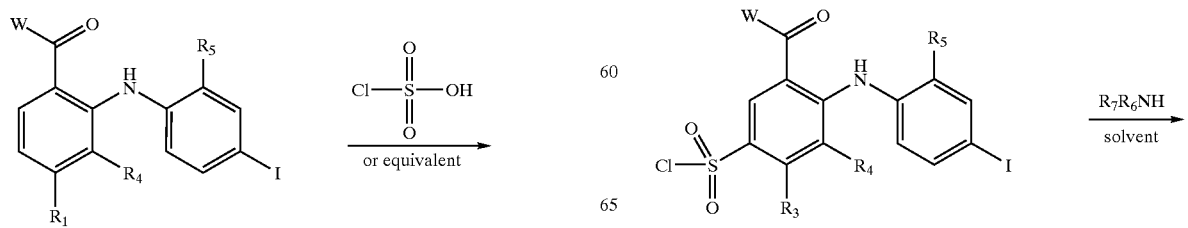

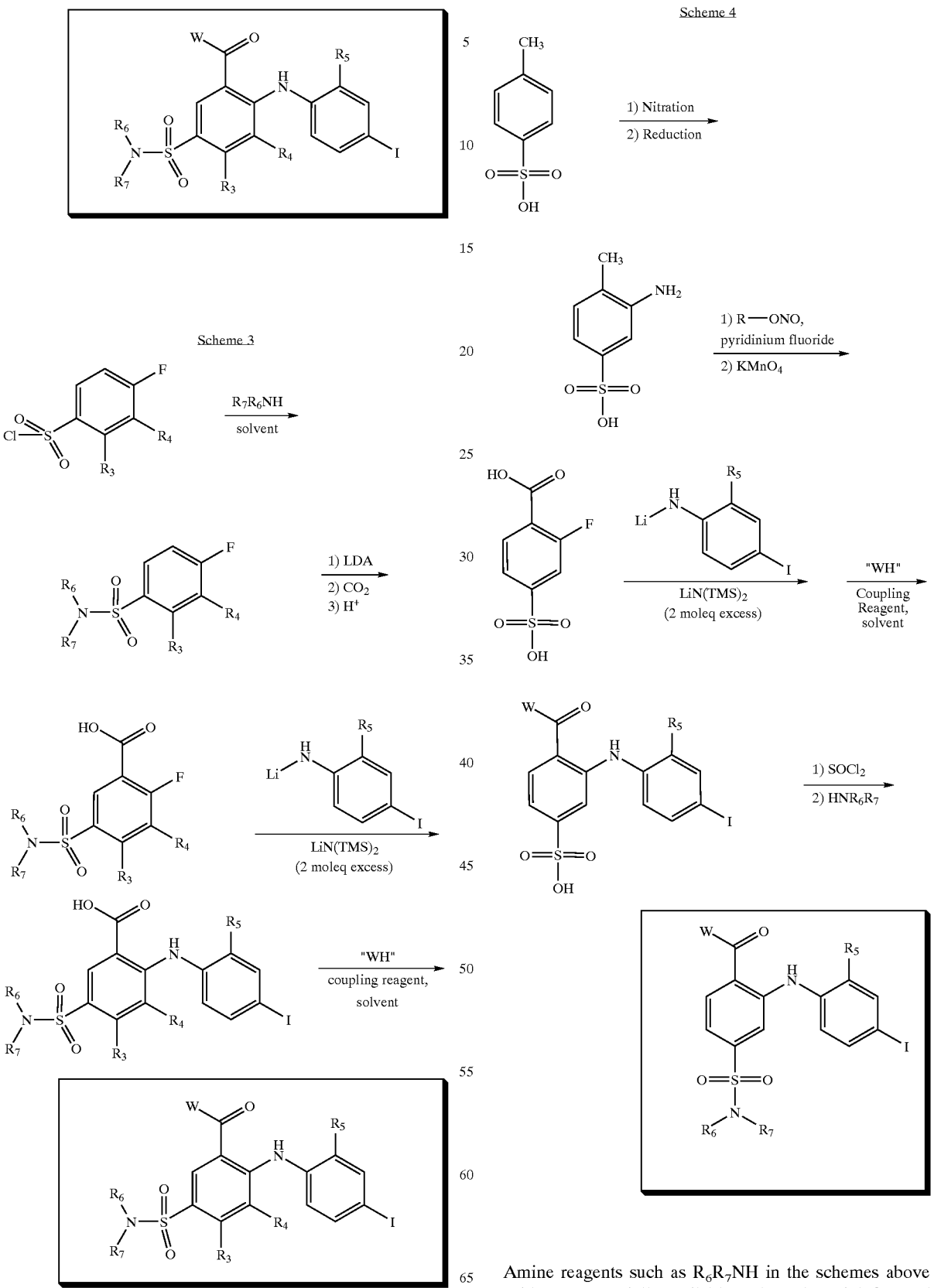
Amine reagents such as $R_6R_7NH$ in the schemes above are either commercially available or through straightforward modification of commercially available intermediates.

Examples of such amine reagents, which can be reacted with the appropriate intermediate in a combinatorial or matrix method, are provided below. For example, in section B (Compounds), starting at page 8, line 16, there are three sets of thirty (one set each for $R_5$=H, Me, and Cl). The table below provides a number (corresponding to order that the name is found in the text; for example, "1" corresponds to compounds 1, 31, and 61 in the list of 90 compounds); the amine reagent name; and a Chemical Abstracts number. Where a PD number is listed, the amine reagent was prepared from commercially available starting materials.

| Number (position in subset of 30) | Amine reagent name | CAS # or PD # |
|---|---|---|
| 1 | 3,3'-dipicolylamine | 1656-94-6 |
| 2 | 3,3'-dipicolylamine | 1656-94-6 |
| 3 | 3-(methylaminomethyl)pyridine | 20173-04-0 |
| 4 | 3-(aminomethyl)pyridine | 3731-52-0 |
| 5 | "N-(3-diethylaminopropyl)-N-(pyridin-3-ylmethyl)amine" | PD 0096419 |
| 6 | 3-(3-pyridylmethylamino)-1-propanol | 6951-00-4 |
| 7 | 3-(ethylaminomethyl)pyridine | PD 0133573 |
| 8 | 2-(3-pyridylmethylamino)ethanol hydrochloride | PD 0018185-0002 |
| 9 | di-(2-picolyl)amine | 1539-42-0 |
| 10 | di-(2-picolyl)amine | 1539-42-0 |
| 11 | 2-(methylaminomethyl)pyridine | PD 0091430 |
| 12 | 2-(aminomethyl)pyridine | 3731-51-9 |
| 13 | 3-(2-pyridylmethylamino)-1-propanol | 6950-99-8 |
| 14 | 2-(2-pyridylmethylamino)ethanol | PD 0018354 |
| 15 | 2-(N-benzylaminomethyl)pyridine | PD 0054372 |
| 16 | 4-(aminomethyl)pyridine | 3731-53-1 |
| 17 | 4-(ethylaminomethyl)pyridine | 33403-97-3 |
| 18 | 4-(methylaminomethyl)pyridine | PD 0111199 |
| 19 | 3-(4-pyridylmethylamino)-1-propanol | 7251-62-9 |
| 20 | 2-(4-pyridylmethylamino)ethanol hydrochloride | PD 0018008-0002 |
| 21 | N-methylaniline | 100-61-8 |
| 22 | aniline | 62-53-3 |
| 23 | 3-aminopyridine | 462-08-8 |
| 24 | aniline | 62-53-3 |
| 25 | 3-amino pyridine | 462-08-8 |
| 26 | 3-(aminomethyl)pyridine | 3731-52-0 |
| 27 | 3,3'-dipicolylamine | 1656-94-6 |
| 28 | 2-(4-pyridylmethylamino)ethanol hydrochloride | PD 0018008-0002 |
| 29 | 3-(methylaminomethyl)pyridine | 20173-04-0 |
| 30 | "N-(3-diethylaminopropyl)-N-(pyridin-3-ylmethyl)amine" | PD 0096419 |

Additional compounds within claim 1 can be made with the following amine reagents. The corresponding CAS number is provided.

| | |
|---|---|
| 2-(methylamino)pyridine | 4597-87-9 |
| 2-benzylaminopyridine | 6935-27-9 |
| 2-allylaminopyridine | 5866-28-4 |
| 2,2'-dipyridylamine | 1202-34-2 |
| 2-anilinopyridine | 6631-37-4 |
| 2-aminopyridine | 504-29-0 |
| 4-aminopyridine | 504-24-5 |
| 2-benzylaminopyridine | 6935-27-9 |
| 2-(4-methoxybenzyl)aminopyridine | 52818-63-0 |
| 2-methylaminopyridine | 4597-87-9 |

Combinatorial Synthesis

The following stock solutions were prepared:
1) An acetonitrile (anhydrous) stock solution 0.05 M in 5-chlorosulfonyl-2,3,4-trifluoro-benzoyl chloride.
2) Acetonitrile (anhydrous) stock solutions 0.05 M in each of the four appropriate hydroxylamine hydrochlorides (see list A) and 0.3 M in 2,6-lutidine.
3) Acetonitrile stock solutions 0.05 M in each of the 25 appropriate amines (see list B). Note that amine salts that were not soluble were also 0.1 M in 2,6-lutidine.
4) Acetonitrile (anhydrous) stock solutions in each of the 3 appropriate anilines (see list C) and 0.88 M in lithium bis(trimethylsilyl)amide (1.0 M in tetrahydrofuran).

An array which treated 4 hydroxylamine hydrochlorides independently with 5-chlorosulfonyl-2,3,4-trifluoro-benzoyl chloride, 25 amines, and 1 aniline was prepared to yield a total of 100 reactions. A liquid handling robot was used to transfer the reagents in such a manner as to insure that all possible combinations were achieved. The appropriate hydroxylamine hydrochloride solution (0.05 mmol, 1 mL) was added to a 2-dram vial, and each vial was treated with 5-chlorosulfonyl-2,3,4-trifluoro-benzoyl chloride solution (0.05 mmol, 1 mL). After 20 minutes the appropriate amine solution (0.05 mmol, 1 mL) was added sequentially. After a further 20 minutes the vials were treated with the solution of 4-iodoaniline (0.055 mmol, 1 mL). The vials were capped and shaken overnight at room temperature. The reactions were quenched with 1 mL of a 1 M aqueous ammonium chloride solution. The vials were concentrated to dryness under a stream of nitrogen and purified by reverse phase HPLC using a 30×100 mm YMC ODS-A (C18) column. The mobile phase was acetonitrile/water (both with 0.05% trifluoroacetic acid) at 25 mL/min and a linear gradient of 10–100% over 6.5 min and then 3.5 min at 100%, detection was at 214 nm.

An array which treated 4 hydroxylamine hydrochlorides independently with 5-chlorosulfonyl-2,3,4-trifluoro-benzoyl chloride, 25 amines, and 1 aniline was prepared to yield a total of 100 reactions. A liquid handling robot was used to transfer the reagents in such a manner as to insure that all possible combinations were achieved. The appropriate hydroxylamine hydrochloride solution (0.05 mmol, 1 mL) was added to a 2-dram vial, and each vial was treated with 5-chlorosulfonyl-2,3,4-trifluoro-benzoyl chloride solution (0.05 mmol, 1 mL). After 20 minutes the appropriate amine solution (0.05 mmol, 1 mL) was added sequentially. After a further 20 minutes the vials were treated with the solution of 4-iodo-2-methylaniline (0.05 mmol, 0.91 mL). The vials were capped and shaken overnight at room temperature. The reactions were quenched with 1 mL of a 1 M aqueous ammonium chloride solution. The vials were concentrated to dryness under a stream of nitrogen and purified by reverse phase HPLC using a 30×100 mm YMC ODS-A (C18) column. The mobile phase was acetonitrile/water (both with 0.05% trifluoroacetic acid) at 25 mL/min and a linear gradient of 10–100% over 6.5 min and then 3.5 min at 100%, detection was at 214 nm.

An array which treated 4 hydroxylamine hydrochlorides independently with 5-chlorosulfonyl-2,3,4-trifluoro-benzoyl chloride, 25 amines, and 1 aniline was prepared to yield a total of 100 reactions. A liquid handling robot was used to transfer the reagents in such a manner as to insure that all possible combinations were achieved. The appropriate hydroxylamine hydrochloride solution (0.05 mmol, 1 mL) was added to a 2-dram vial, and each vial was treated with 5-chlorosulfonyl-2,3,4-trifluoro-benzoyl chloride solution (0.05 mmol, 1 mL). After 20 minutes the appropriate amine solution (0.05 mmol, 1 mL) was added sequentially. After a further 20 minutes the vials were treated with the solution of 2-chloro-4-iodoaniline (0.05 mmol, 0.91 mL). The vials were capped and shaken overnight at room temperature. The reactions were quenched with 1 mL of a 1 M aqueous ammonium chloride solution. The vials were concentrated to dryness under a stream of nitrogen and purified by reverse phase HPLC using a 30×100 mm YMC ODS-A (C18) column. The mobile phase was acetonitrile/water (both with 0.05% trifluoroacetic acid) at 25 mL/min and a linear gradient of 10–100% over 6.5 min and then 3.5 min at 100%, detection was at 214 nm.

Combinatorial Synthesis

Table of Example Reagents

List A-Hydroxylamines
1. O-methyl-hydroxylamine
2. O-allyl-hydroxylamine hydrochloride monohydrate (Aldrich)
3. O-cyclopropylmethyl-hydroxylamine hydrochloride
4. O-(2-morpholin-4-yl-ethyl)-hydroxylamine hydrochloride List B-Amines
1. dimethylamine
2. diethylamine
3. isopropyl-methyl-amine
4. diisopropylamine
5. methylhydrazine
6. 1-methylpiperazine
7. N,N-diethyl-N'-methylethane-1,2-diamine
8. benzylmethylamine
9. dibenzylamine
10. methyl-phenyl-amine
11. allyl-methyl-amine
12. methyl-prop-2-ynyl-amine
13. methylamino-acetonitrile hydrochloride
14. 1-(4-fluoro-phenyl)-piperazine
15. furan-2-ylmethyl-methyl-amine
16. piperidine-3-carboxylic acid amide
17. methyl-phenethyl-amine
18. methyl-(2-pyridin-2-yl-ethyl)-amine
19. N,N,N'-trimethyl-propane-1,3-diamine
20. methyl-(1-methyl-piperidin-4-yl)-amine
21. 1-pyridin-2-yl-piperazine
22. bis-(2-methoxy-ethyl)-amine
23. N'-benzyl-N,N-dimethyl-ethane-1,2-diamine
24. methylamino-acetic acid tert-butyl ester hydrochloride
25. O,N-dimethyl-hydroxylamine hydrochloride List C-Anilines
1. 4-iodoaniline
2. 2-chloro-4-iodoaniline
3. 4-iodo-2-methylaniline

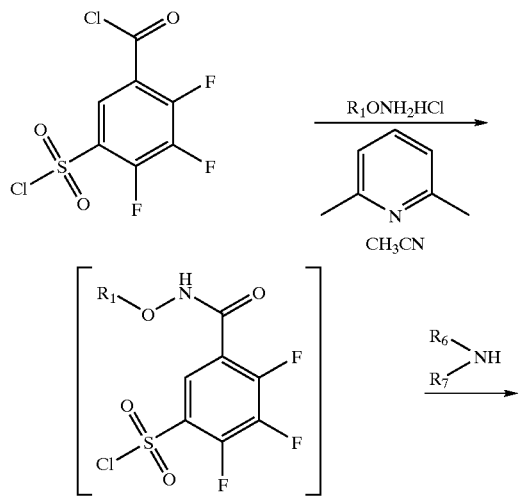

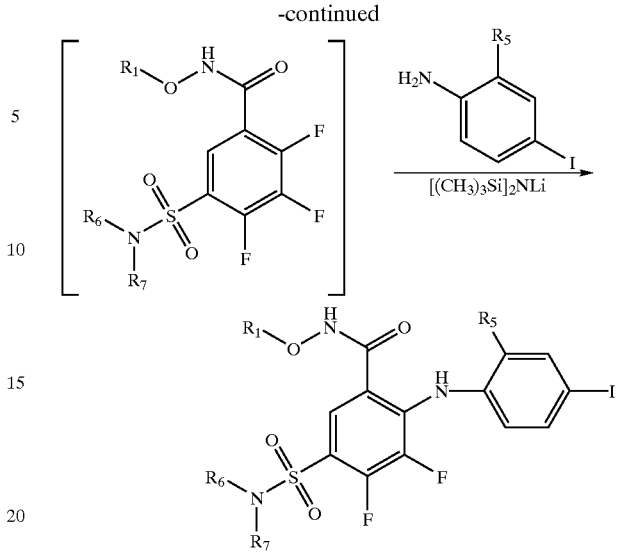

D. Uses

The disclosed compositions are useful as both prophylactic and therapeutic treatments for diseases or conditions as provided in the Summary section, as well as diseases or conditions modulated by the MEK cascade. Examples include stroke, heart failure, osteoarthritis, rheumatoid arthritis, organ transplant rejection, and a variety of tumors such as ovarian, lung, pancreatic, brain, prostatic, renal, and colorectal.

1. Dosages

Those skilled in the art will be able to determine, according to known methods, the appropriate dosage for a patient, taking into account factors such as age, weight, general health, the type of symptoms requiring treatment, and the presence of other medications. In general, an effective amount will be between 0.1 and 1000 mg/kg per day, preferably between 1 and 300 mg/kg body weight, and daily dosages will be between 10 and 5000 mg for an adult subject of normal weight. Capsules, tablets or other formulations (such as liquids and film-coated tablets) may be of between 5 and 200 mg, such as 10, 15, 25, 35, 50 mg, 60 mg, and 100 mg and can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels, or cream), and by inhalation (a buccal or nasal spray).

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption acccelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

3. Related Compounds

The invention provides the disclosed compounds and closely related, pharmaceutically acceptable forms of the disclosed compounds, such as salts, esters, amides, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$ alkyl, cycloalkyl, aryl, heteroaryl, or non-aromatic heterocyclic), amino acid addition salts, esters, and amides which are within a reasonable benefit/risk ratio, pharmacologically effective, and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge, et al., "Pharmaceutical Salts," *J. Pharm. Sci.*, 1977, 66:1–19 which is incorporated herein by reference. Representative pharmaceutically acceptable amides of the invention include those derived from ammonia, primary $C_{1-6}$ alkyl amines and secondary di($C_{1-6}$ alkyl) amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Hydroxyl protecting groups include: ethers, esters, and protection for 1,2- and 1,3-diols. The ether protecting groups include: methyl, substituted methyl ethers, substituted ethyl ethers, substituted benzyl ethers, silyl ethers and conversion of silyl ethers to other functional groups.

Substituted Methyl Ethers

Substituted methyl ethers include: methoxymethyl, methylthiomethyl, t-utylthiomethyl, (phenyldimethylsilyl) methoxymethyl, benzyloxymethyl, p-ethoxybenzyl- oxymethyl, (4-methoxyphenoxy) methyl, guaiacolmethyl, t-butoxymethyl, 4-pentenyloxymethyl, siloxymethyl, 2-methoxyethoxymethyl, 2,2,2-trichloroethoxymethyl, bis (2-chloro-ethoxy)methyl, 2-(trimethylsilyl)-ethoxymethyl, tetrahydropyranyl, 3-bromotetrahydro-pyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl, and 2,3,3a,4,5,6,7,7a-octahydro-7,8,8-trimethyl-4,7-ethanobenzofuran-2-yl.

Substituted Ethyl Ethers

Substituted ethyl ethers include: 1-ethoxyethyl, 1-(2, chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilyethyl, 2-(phenylselenyl)ethyl, t-butyl, allyl, p-chlorophenyl, p-methoxyphenyl, 2,4-dinitrophenyl, and benzyl.

Substituted Benzyl Ethers

Substituted benzyl ethers include: p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri-(p-methoxyphenyl) methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl) methyl, 4,4',4"tris (benzoyloxyphenyl)methyl, 3-(imidazol-1-ylmethyl)bis(4', 4"-dimethoxyphenyl)-methyl, 1,1-bis(4-methoxyphenyl)-1'-pyrenylmethyl, 9-anthryl, 9-(9-phenyl) xanthenyl, 9-(9-phenyl-10-oxo) anthryl, 1,3-benzodithiolan-2-yl, and benzisothiazolyl S,S-dioxido.

Silyl Ethers

Silyl ethers include: trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxy-phenylsilyl.

Esters

Esters protecting groups include: esters, carbonates, assisted cleavage, miscellaneous esters, and sulfonates.

Esters

Examples of protective esters include: formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate (levulinate), 4,4-(ethylenedithio) pentanoate, pivaloate, adamantoate, crotonate, 4-methoxycrotonate, benzoate, p-phenylbenzoate, and 2,4,6-trimethylbenzoate (mesitoate).

Carbonates

Carbonates include: methyl, 9-fluorenylmethyl, ethyl, 2,2, 2-trichloroethyl, 2-(trimethylsilyl) ethyl, 2-(phenylsulfonyl) ethyl, 2-(triphenylphosphonio) ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage protecting groups include: 2-iodobenzoate, 4-azido-butyrate, 4-nitro-4-methylpentanoate, o-(dibromomethyl) benzoate, 2-formylbenzene-sulfonate, 2-(methylthiomethoxy) ethyl carbonate, 4-(methylthiomethoxymethyl) benzoate, and 2-(methylthiomethoxymethyl) benzoate.

Miscellaneous Esters

In addition to the above classes, miscellaneous esters include: 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate (tigloate), o-(methoxycarbonyl) benzoate, p-P-benzoate, α-naphthoate, nitrate, alkyl N,N,N', N'-tetramethyl-phosphorodiamidate, N-phenylcarbamate, borate, dimethylphosphinothioyl, and 2,4-dinitrophenylsulfenate.

Sulfonates

Protective sulfates includes: sulfate, methanesulfonate (mesylate), benzylsulfonate, and tosylate.

Protection for 1,2- and 1,3-Diols

The protection for 1,2 and 1,3-diols group includes: cyclic acetals and ketals, cyclic ortho esters, and silyl derivatives.

Cyclic Acetals and Ketals

Cyclic acetals and ketals include: methylene, ethylidene, 1-t-butylethylidene, 1-phenylethylidene, (4-methoxyphenyl) ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Cyclic ortho esters include: methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino) benzylidene derivative, and 2-oxacyclopentylidene.

Protection for the Carboxyl Group Esters

Ester protecting groups include: esters, substituted methyl esters, 2-substituted ethyl esters, substituted benzyl esters, silyl esters, activated esters, miscellaneous derivatives, and stannyl esters.

Substituted Methyl Esters

Substituted methyl esters include: 9-fluorenylmethyl, methoxymethyl, methylthiomethyl, tetrahydropyranyl, tetrahydrofuranyl, methoxyethoxymethyl, 2-(trimethylsilyl) ethoxy-methyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

2-Substituted ethyl esters include: 2,2,2-trichloroethyl, 2-haloethyl, |-chloroalkyl, 2-(trimethylsily)ethyl, 2-methylthioethyl, 1,3-dithianyl-2-methyl, 2(p-nitrophenylsulfenyl)-ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsily)-2-buten-1-yl, cinnamyl, α-methylcinnamyl, phenyl, p-(methylmercapto)-phenyl, and benzyl.

Substituted Benzyl Esters

Substituted benzyl esters include: triphenylmethyl, diphenylmethyl, bis(o-nitrophenyl)methyl, 9-anthrylmethyl, 2-(9,10-dioxo)anthrylmethyl, 5-dibenzo-suberyl, 1-pyrenylmethyl,2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, and 4-P-benzyl.

Silyl Esters

Silyl esters include: trimethylsilyl, triethylsilyl, t-butyldimethylsilyl, i-propyldimethylsilyl, phenyldimethylsilyl, and di-t-butylmethylsilyl.

Miscellaneous Derivatives

Miscellaneous derivatives includes: oxazoles, 2-alkyl-1, 3-oxazolines, 4-alkyl-5-oxo-1,3-oxazolidines, 5-alkyl-4-oxo-1,3-dioxolanes, ortho esters, phenyl group, and pentaminocobalt(III) complex.

Stannyl Esters

Examples of stannyl esters include: triethylstannyl and tri-n-butylstannyl.

Amides and Hydrazides

Amides include: N,N-dimethyl, pyrrolidinyl, piperidinyl, 5,6-dihydrophenanthridinyl, o-nitroanilides, N-7-nitroindolyl, N-8-nitro-1,2,3,4-tetrahydroquinolyl, and p-P-benzenesulfonamides. Hydrazides include: N-phenyl, N,N'-diisopropyl and other dialkyl hydrazides.

Protection for the Amino Group

Carbamates

Carbamates include: carbamates, substituted ethyl, assisted cleavage, photolytic cleavage, urea-type derivatives, and miscellaneous carbamates.

Carbamates

Carbamates include: methyl and ethyl, 9-fluorenylmethyl, 9-(2-sulfo)fluorenylmethyl, 9-(2,7-dibromo) fluorenylmethyl, 2,7-di-t-butyl-[9-(10,10-dioxo-10,10,10, 10-tetrahydro-thioxanthyl)]methyl, and 4-methoxyphenacyl.

Substituted Ethyl

Substituted ethyl protective groups include: 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'-and 4'-pyridyl)ethyl, 2-(N,N-icyclohexylcarboxamido)-ethyl, t-butyl, 1-adamantyl, vinyl, allyl, 1-isopropylallyl, connamyl, 4-nitrocinnamyl, quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, and diphenylmethyl.

Assisted Cleavage

Protection via assisted cleavage includes: 2-methylthioethyl, 2-methylsulfonylethyl, 2-(p-toluenesulfonyl)ethyl, [2-(1,3-dithianyl)]methyl, 4-methylthiophenyl, 2,4-dimethyl-thiophenyl, 2-phosphonioethyl, 2-triphenylphosphonioisopropyl, 1,1-dimethyl-2cyanoethyl, m-chloro-p-acyloxybenzyl, p-(dihydroxyboryl)benzyl, 5-benzisoxazolyl-methyl, and 2-(trifluoromethyl)-6-chromonylmethyl.

Photolytic Cleavage

Photolytic cleavage methods use groups such as: m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of of urea-type derivatives include: phenothiazinyl-(10)-carbonyl derivative, N'-p-toluenesulfonylaminocarbonyl, and N'-phenylaminothiocarbonyl.

Miscellaneous Carbamates

In addition to the above, miscellaneous carbamates include: t-amyl, S-benzyl thiocarbamate, p-cyanobenzyl, cyclobutyl, cyclohexyl, cyclopentyl, cyclopropylmethyl, p-decyloxy-benzyl, diisopropylmethyl, 2,2-dimethoxy-carbonylvinyl, o-(N,N-dimethyl-carboxamido)-benzyl, 1,1- dimethyl-3(N,N-dimethylcarboxamido)propyl, 1,1-dimethyl-propynyl, di(2-pyridyl)methyl, 2-furanylmethyl, 2-iodoethyl, isobornyl, isobutyl, isonicotinyl, p(p'-methoxyphenylazo)benzyl, 1-methylcyclobutyl, 1-methylcyclohexyl, 1-methyl-1-cyclopropylmethyl, 1-methyl-(3,5-dimethoxyphenyl)ethyl, 1-methyl-1(p-henylazophenyl)-ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)-benzyl, and 2,4,6-trimethylbenzyl.

Amides
Amides
Amides includes: N-formyl, N-acetyl, N-chloroacetyl, N-trichloroacetyl, N-trifluoroacetyl, N-phenylacetyl, N-3-phenylpropionyl, N-picolinoyl, N-3-pyridyl-carboxamide, N-benzoylphenylalanyl derivative, N-benzoyl, and N-p-phenylbenzoyl.

Assisted Cleavage
Assisted cleavage groups include: N-o-nitrophenylacetyl, N-o-nitrophenoxyacetyl, N-acetoacetyl, (N'-dithiobenzyloxycarbonylamino)acetyl, N-3-(p-hydroxphenyl) propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives
Cyclic imide derivatives include: N-phthalimide, N-dithiasuccinoyl, N-2,3-diphenyl-maleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special —NH Protective Groups
Protective groups for —NH include: N-alkyl and N-aryl amines, imine derivatives, enamine derivatives, and N-hetero atom derivatives (such as N-metal, N-N,N-P, N-Si, and N-S), N-sulfenyl, and N-sulfonyl.

N-Alkyl and N-Aryl Amines
N-alkyl and N-aryl amines include: N-methyl, N-allyl, N-[2-(trimethylsilyl)ethoxyl]-methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives
Imine derivatives include: N-1,1-dimethylthiomethylene, N-benzylidene, N-p-methoxybenzylidene, N-diphenylmethylene, N-[(2-pyridyl)mesityl]methylene, N-(N',N'-dimethylaminomethylene), N,N'-isopropylidene, N-p-nitrobenzylidene, N-salicylidene, N-5-chlorosalicylidene, N-(5-chloro-2-hydroxyphenyl)phenylmethylene, and N-cyclohexylidene.

Enamine Derivative
An example of an enamine derivative is N-(5,5-dimethyl-3-oxo-1-cyclohexenyl).

N-Hetero Atom Derivatives
N-metal derivatives include: N-borane derivatives, N-diphenylborinic acid derivative, N-[phenyl(pentacarbonylchromium- or -tungsten)]carbenyl, and N-copper or N-zinc chelate. Examples of N-N derivatives include: N-nitro, N-nitroso, and N-oxide. Examples of N-P derivatives include: N-diphenylphosphinyl, N-dimethylthiophosphinyl, N-diphenylthiophosphinyl, N-dialkyl phosphoryl, N-dibenzyl phosphoryl, and N-diphenyl phosphoryl. Examples of N-sulfenyl derivatives include: N-benzenesulfenyl, N-o-nitrobenzenesulfenyl, N-2,4-dinitrobenzenesulfenyl, N-pentachlorobenzenesulfenyl, N-2-nitro-4-methoxy-benzenesulfenyl, N-triphenylmethylsulfenyl, and N-3-nitropyridinesulfenyl.

N-sulfonyl derivatives include: N-p-toluenesulfonyl, N-benzenesulfonyl, N-2,3,6-trimethyl-4-methoxybenzenesulfonyl, N-2,4,6-trimethoxy-benzenesulfonyl, N-2,6-dimethyl-4-methoxy-benzenesulfonyl, N-pentamethylbenzenesulfonyl, N-2,3,5,6-tetramethyl-4-methoxybenzene-sulfonyl, N-4-methoxybenzenesulfonyl, N-2,4,6-trimethylbenzene-sulfonyl, N-2,6-dimethoxy-4-methylbenzenesulfonyl, N-2,2,5,7,8-pentamethylchroman-6-sulfonyl, N-methanesulfonyl, N-β-trimethylsilylethanesulfonyl, N-9-anthracenesulfonyl, N-4-(4',8'-dimethoxynaphthylmethyl)-benzenesulfonyl, N-benzylsulfonyl, N-trifluoromethylsulfonyl, and N-phenacylsulfonyl.

Disclosed compounds which are masked or protected may be prodrugs, compounds metabolized or otherwise transformed in vivo to yield a disclosed compound, e.g., transiently during metabolism. This transformation may be a hydrolysis or oxidation which results from contact with a bodily fluid such as blood, or the action of acids, or liver, gastrointestinal, or other enzymes.

Features of the invention are further described in the examples below.

E. EXAMPLES

Example 1

Preparation of 2-(2-chloro-4-iodo-phenylamino)-5-dimethylsulfamoyl-3,4-difluoro-benzoic acid methyl ester (APK $IC_{50}$=222 nM)

Step a: Preparation of 1-dimethylsulfamoyl-2,3,4-trifluorobenzene

To a gently stirring solution comprised of 2,3,4-trifluorobenzenesulfonyl chloride (5.70 g, 0.0247 mol) in 1,2-dichloroethane (200 ml) was introduced by bubbling gaseous anhydrous dimethylamine. The mixture became cloudy after several minutes and was subsequently washed with water (200 ml), 6 N aqueous hydrochloric acid (200 ml), brine (200 ml), was dried over anhydrous magnesium sulfate, and was concentrated in vacuo to obtain a yellow oil. The crude product was purified by flash chromatography. Elution with dichloromethane afforded 3.40 g of a white solid; 58% yield; $^1$H-NMR (400 MHz; $CDCl_3$) δ7.63–7.56 (m, 1H), 7.12–7.04 (m, 1H), 2.812 (s, 3H), 2.807 (s, 3H); $^{19}$F-NMR (376 MHz; $CDCl_3$) δ–124.91 to –125.03 (m), –127.98 to –128.03 (m), –156.41 to –156.53.

Step b: Preparation of 5-dimethylsulfamoyl-2,3,4-trifluorobenzoic Acid

To a cold (–78° C.) stirring solution comprised of 1-dimethylsulfamoyl-2,3,4-trifluorobenzene in anhydrous tetrahydrofuran (60 ml) under a nitrogen atmosphere was added a commercially available lithium diisopropylamide solution (Aldrich, 2.0 M in tetrahydrofuran/heptane/ethylbenzene, 7.5 ml, 0.0150 mol). After stirring for about ten minutes, the purple solution was transferred via canula to a cold, stirring, saturated carbon dioxide in diethyl ether solution (200 ml). The reaction mixture took on a dull burgundy color. The cold bath was removed and the reaction mixture warmed to ambient temperature over one hour. The mixture was then carefully quenched with 10% aqueous hydrochloric acid (200 ml). The layers were separated. The organic phase was extracted twice (200, 100 ml portions) with 10% (wt.) aqueous sodium hydroxide. The combined aqueous alkaline extracts were treated with concentrated aqueous hydrochloric acid (100 ml) to pH 0. A white precipitate formed. The suspension was allowed to cool, then was extracted with diethyl ether (600 ml). The organic extract was dried over anhydrous magnesium sulfate and was concentrated in vacuo to afford 2.70 g of an off-white solid; 67.5% yield; mp 225–228° C.; $^1$H-NMR (400 MHz; DMSO) δ14.08 (broad s, 1H), 8.02–7.97 (m, 1H), 2.75 (s, 3H), 2.74 (s, 3H) $^{19}$F-NMR (376 MHz; DMSO) δ–122.50 to –122.63 (m), –122.95 to –123.08 (m), –154.49 to –154.61 (m); MS (APCI+) 284 (M+1, 22), 238 (100); (APCI–) 282 (M–1, 85), 259 (94), 238 (46), 216 (91), 195 (100); IR (KBr) 1702 cm$^{-1}$; Anal. calcd/found for: $C_9H_8F_3NO_4S$ C, 38.17/38.40; H, 2.85/2.90; N, 4.95/4.80; F, 20.12/19.75; S, 11.32/11.12.

Step c: Preparation of 5-dimethylsulfamoyl-2,3,4-trifluoro-benzoic acid methyl ester The solid 5-dimethylsulfamoyl-2,3,4-trifluoro-benzoic acid (1.47 g, 0.00519 mol) and p-toluenesulfonic acid catalyst (17.1 mg) were dissolved in methanol (125 ml). The stirring mixture was brought to reflux under a nitrogen atmosphere for 51 hours. The reaction mixture was concentrated in vacuo to give a solid. The product was partitioned between diethyl ether (200 ml) and saturated aqueous potassium carbonate (75 ml). The layers were separated and the organic phase was washed with water (75 ml), brine (75 ml), was dried over anhydrous potassium carbonate, and was concentrated in vacuo to afford 0.15 g of an off-white solid; 10% yield; $^1$H-NMR (400 MHz; CDCl$_3$) δ8.23–8.19 (m, 1H), 3.92 (s, 3H), 2.83 (s, 6H); $^{19}$F-NMR (376 MHz; CDCl$_3$) δ–120.79 to –121.02 (m), –153.69 to –153.80.

Step d: Preparation of 2-(2-chloro-4-iodo-phenylamino)-5-dimethylsulfamoyl-3,4-difluoro-benzoic acid methyl ester To a stirring cold (–78° C.) solution comprised of 2-chloro-4-iodoaniline (0.143 g, 5.64×10$^{-4}$ mol) in anhydrous tetrahydrofuran (5 ml) under a nitrogen atmosphere was added a commercially available lithium diisopropylamide solution (Aldrich, 2.0 M in tetrahydrofuran/heptane/ethylbenzene, 0.300 ml, 6.0×10$^{-4}$ mol). After stirring for 5 minutes, a solution comprised of 5-dimethylsulfamoyl-2,3,4-trifluoro-benzoic acid methyl ester (0.15 g, 5.0×10$^{-4}$ mol) in tetrahydrofuran (10 ml) was added via syringe. The cold bath was removed and the reaction mixture was stirred for 2 hours. The reaction mixture was then partitioned between diethyl ether (125 ml) and saturated aqueous sodium bicarbonate (125 ml). The aqueous bicarbonate phase was extracted with an additional portion (125 ml) of diethyl ether. The combined organic phases were dried over anhydrous magnesium sulfate and concentrated in vacuo to give a yellow oil. The oil was crystallized from heptane-ethyl acetate to afford 0.060 g of an off-white powder; 23% yield; mp 154–156° C.; $^1$H-NMR (400 MHz; CDCl$_3$) δ9.74 (s, 1H), 8.30 (d, 1H, J=7.1 Hz), 7.72 (s, 1H), 7.49 (d, 1H, J=8.3 Hz), 6.73–6.69 (m, 1H), 3.92 (s, 3H), 2.84 (s, 3H), 2.83 (s, 3H); $^{19}$F-NMR (376 MHz; CDCl$_3$) δ–123.90 (d), –139.55 (d).

Example 2

Preparation of 2-(2-chloro-4-iodo-phenylamino)-N-cyclopropylmethoxy-3,4-difluoro-5-sulfamoyl-benzamide (PD 219622)

Step a: Preparation of 1-bis-(4-methoxybenzyl)sulfamoyl-2,3,4-trifluorobenzene

To a stirring solution comprised of bis-4-methoxybenzylamine (2.5 g, 9.7×10$^{-3}$ mol) and diisopropylethylamine (1.7 ml, 9.7×10$^{-3}$ mol) in dichloromethane (50 ml) at 0° C. under nitrogen atmosphere was added liquid 2,3,4-trifluorobenzenesulfonyl chloride (2.26 g, 9.5×10$^{-3}$ mol) directly. The mixture was stirred cold for ten minutes. The ice-water bath was removed and the mixture was stirred for an additional 15 minutes and was then diluted with dichloromethane to 350 ml volume and was washed with saturated aqueous ammonium chloride (200 ml). The organic phase was dried (MgSO$_4$) and concentrated in vacuo to afford 4.99 g of a sticky white solid. The crude product was recrystallized from hexanes-acetone to afford 3.00 g of white needles; 70% yield; mp 87–90° C.; $^1$H-NMR (400 MHz; CDCl$_3$) δ7.64–7.58 (m, 1H), 7.04–6.99 (m, 1H), [6.97 (d, 4H, J=8.5 Hz), 6.75 (d, 4H, J=8.8 Hz) AB q], 4.33 (s, 4H), 3.76 (s, 6H); $^{19}$F-NMR (376 MHz; CDCl$_3$) δ–125.44 to –125.56 (m), –128.61 to –128.72 (m), –156.91 to –157.03 (m); MS (APCI+) 121 (M–330, 100); (APCI–) 330 (M–121, 18), 195 (M–256, 100); IR (KBr) 1612, 1517, 1506, 1465, 1258, 1240, 1156, 1037, 1030 cm$^{-1}$; Anal. calcd/found for: $C_{22}H_{20}F_3NO_4S$ C, 58.53/57.98; H, 4.47/4.61; N, 3.10/2.85.

Step a: Preparation of 5-bis-(4-methoxybenzyl)sulfamoyl-2,3,4-trifluorobenzoic acid To a stirring solution comprised of 1-bis-(4-methoxybenzyl)sulfamoyl-2,3,4-trifluorobenzene (2.95 g, 6.5×10$^{-3}$ mol) in tetrahydrofuran (60 ml) at –78° C. was added a solution comprised of 2.0 M lithium diisopropylamide in tetrahydrofuran/heptane/ethylbenzene (Aldrich, 3.35 ml, 6.7×10$^{-3}$ mol). After several minutes of stirring, the dark solution was transferred via canula over five minutes to a stirring solution comprised of carbon dioxide (excess) in diethyl ether at –78° C. A white precipitate immediately formed. The cold bath was removed and the reaction mixture was stirred at ambient temperature for 18 hours. The reaction mixture was quenched with 200 ml of dilute aqueous hydrochloric acid. The layers were separated and the organic phase was dried (MgSO$_4$) and concentrated in vacuo to give 2.82 g of an off-white solid. Recrystallization from dichloromethane (150 ml) afforded 2.10 g of the white powder product; 65% yield; mp 158–161° C.; $^1$H-NMR (400 MHz; DMSO) δ7.80–7.76 (m, 1H), 7.05–6.74 (AB q, 8H, J=8.6 Hz), 4.33 (s, 4H), 3.66 (s, 6H); $^{19}$F-NMR (376 MHz; DMSO) δ–123.28 to –123.36 (m), –124.12 to –124.21 (m), –155.41 to –155.53 (m); MS (APCI–) 494 (M–1, 47), 216 (89), 195 (100); IR (KBr) 3420, 2954, 2838, 1695, 1613, 1512, 1347, 1238, 1152, 1079 cm$^{-1}$; Anal. calcd/found for: $C_{23}H_{20}F_3NO_6S$ C, 55.76/55.85; H, 4.07/4.02; N, 2.83/2.71; F, 11.50/11.41; S, 6.47/6.25.

Step c: Preparation of 5-bis-(4-methoxybenzyl)sulfamoyl-2-(2-chloro-4-iodophenylamino)-3,4-difluorobenzoic acid (PD 215729)

To a stirring solution comprised of 2-chloro-4-iodoaniline (0.53 g, 2.0×10$^{-3}$ mol) in tetrahydrofuran (10 ml) at –78° C. under a nitrogen atmosphere was added a solution comprised of 1.0 M lithium bis(trimethylsilyl)amide in tetrahydrofuran (Aldrich, 4.1 ml, 4.1×10$^{-3}$ mol). Within several minutes the solution became a thick light-green suspension. To this mixture was added a solution comprised of lithium 5-bis-(4-methoxybenzyl)sulfamoyl-2,3,4-trifluorobenzoate in tetrahydrofuran, which was prepared by adding 2.0 ml of the Aldrich lithium bis(trimethylsilyl)amide solution (0.0020 mmol) to a solution comprised of 5-bis-(4-methoxybenzyl)sulfamoyl-2,3,4-trifluorobenzoic acid (1.00 g, 2.0×10$^{-3}$ mol) in tetrahydrofuran (10 ml) at −78° C. The reaction mixture was stirred for 15 minutes and was then concentrated in vacuo to a crude semisolid. The semisolid was taken up into diethyl ether (250 ml) and was washed with 1% aqueous hydrochloric acid (150 ml). The ether phase was then washed with neutral water (200 ml, pH 4 after wash), a second portion of water (200 ml, pH 6 after wash), and brine (200 ml). The organic phase was then dried (MgSO$_4$) and was concentrated in vacuo to give 1.88 g of a sticky residue which was crystallized from toluene-heptane to afford 1.12 g of an off-white powder; 76% yield; mp 162–166° C.; $^1$H-NMR (400 MHz; DMSO) δ9.86 (s, 1H), 7.92 (d, 1H, J=6.8 Hz), 7.86 (d, 1H, J=1.7 Hz), 7.60 (dd, 1H, J=8.5, 1.7 Hz), 7.06–7.04/6.78–6.75 (AB q, 8H, J=8.5 Hz), 6.93–6.89 (m, 1H), 4.31 (s, 4H), 3.66 (s, 6H); $^{19}$F-NMR (376 MHz; DMSO) δ−127.22 (d), −141.36 (d); MS (APCI+) 729 (M+1, 1), 256 (50), 121 (100); (APCI−) 727 (M−1, 100); IR (KBr) 1698, 1673, 1513, 1251 cm$^{-1}$; Anal. calcd/found for: C$_{29}$H$_{24}$ClF$_2$IN$_2$O$_6$S C, 47.78/47.93; H, 3.32/3.33; N, 3.84/3.80; Cl, 4.86/4.84; F, 5.21/5.46; I,17.41/17.16; S, 4.40/4.29.

Step d: Preparation of 5-bis-(4-methoxybenzyl)sulfamoyl-2-(2-chloro-4-iodophenylamino)-N-cyclopropylmethoxy-3,4-difluorobenzamide (PD 218774)

To a stirring solution comprised of 5-bis-(4-methoxybenzyl)sulfamoyl-2-(2-chloro-4-iodophenylamino)-3,4-difluorobenzoic acid (0.935 g, 1.28× 10$^{-3}$ mol), cyclopropylmethoxyamine hydrochloride (0.175 g, 1.42×10$^{-3}$ mol), and diisopropylethylamine (0.75 ml, 4.26×10$^{-3}$ mol) in a 1:1 v/v tetrahydrofuran-dichloromethane mixture (50 ml) was added solid PyBOP ([benzotriazolyloxy]tripyrrolidino phosphonium hexafluorophosphate, Advanced ChemTech, 0.76 g, 1.46× 10$^{-3}$ mol). The reaction mixture was stirred for one hour, was then evaporated to a crude residue which was purified by flash silica column chromatography. Elution with a gradient (25% dichloromethane to 75% dichloromethane in hexanes) afforded 0.63 g of the off-white powder product; 62% yield; mp 70>300° C.; $^1$H-NMR (400 MHz; DMSO) δ11.92 (s, 1H), 9.35 (s, 1H), 7.60 (s, 1H), 7.50–7.45 (m, 1H), 7.34 (d, 1H, J=8.5 Hz), 6.82–6.54 (AB q, 8H, J=8.3 Hz), 6.59–6.54 (m, 1H), 4.09 (s, 4H), 3.46 (s, 6H), 0.90–0.80 (m, 1H), 0.30–0.25 (m, 2H), 0.03–0.00 (m, 2H); $^{19}$F-NMR (376 MHz; DMSO) δ−129.05 (s), −140.23 (d, J=18.3 Hz); MS (APCI+) 798 (M+1, 70); (APCI−) 796 (M−1, 15), 726 (50), 131 (100); IR (KBr) 1642, 1611, 1584, 1513, 1478 cm$^{-1}$; Anal. calcd/found for: C$_{33}$H$_{31}$ClF$_2$IN$_3$O$_6$S C, 49.67/49.88; H, 3.92/3.95; N, 5.27/5.19.

Step e: Preparation of 2-(2-chloro-4-iodophenylamino)-N-cyclopropylmethoxy-3,4-difluoro-5-sulfamoyl-benzamide (PD 219622)

A reaction solution comprised of 5-bis-(4-methoxybenzyl)sulfamoyl-2-(2-chloro-4-iodo-phenylamino)-N-cyclopropylmethoxy-3,4-difluorobenzamide (0.1010 g, 1.266×10$^{-4}$ mol) in trifluoroacetic acid (4 ml) was stirred at ambient temperature for 24 hours. The mixture was vacuum filtered and the precipitate rinsed with hexanes to afford 28.6 mg of a pale lavender powder; 42% yield; mp 219–227° C. DEC; $^1$H-NMR (400 MHz; DMSO) δ11.89 (s, 1H), 9.08 (s, 1H), 7.60 (s, 3H), 7.55 (d, 1H, J=6.9 Hz), 7.32 (d, 1H, J=8.6 Hz), 6.63–6.59 (m, 1H), 3.40 (d, 2H, J=6.6 Hz), 0.90–0.80 (m, 1H), 0.30–0.26 (m, 2H), 0.05–0.00 (m, 2H); $^{19}$F-NMR (376 MHz; DMSO) δ−130.61 (s), −140.38 (d, J=21.4 Hz); MS (APCI+) 558 (M+1, 70), 282 (100); (APCI−) 556 (M−1, 73), 486 (100); IR (KBr) 3390, 3283, 1652, 1513, 1477, 1163 cm$^{-1}$; Anal. calcd/found for: C$_{17}$H$_{15}$ClF$_2$IN$_3$O$_4$S 0.1 C$_2$HF$_3$O$_2$ C, 36.30/36.31; H, 2.67/2.55; N, 7.38/7.00.

Example 3

Preparation of 2-(2-chloro-4-iodo-phenylamino)-3,4-difluoro-N-hydroxy-5-sulfamoyl-benzamide (PD 224213)

To a stirring solution comprised of 5-bis-(4-methoxybenzyl)sulfamoyl-2-(2-chloro-4-iodophenylamino)-3,4-difluorobenzoic acid (0.67 g, 9.2× 10$^{-4}$ mol), O-(tetrahydro-2H-pyran-2-yl)-hydroxylamine (0.113 g, 9.65×10$^{-4}$ mol), and diisopropylethylamine (0.50 ml, 2.9×10$^{-3}$ mol) in a 1:1 v/v tetrahydrofuran-dichloromethane mixture (20 ml) was added solid PyBOP ([benzotriazolyloxy]tripyrrolidino phosphonium hexafluorophosphate, Advanced ChemTech, 0.52 g, 1.0× 10$^{-3}$ mol). The reaction mixture was stirred for 30 minutes, was concentrated in vacuo to a yellow oil, and was crystallized from methanol to afford 0.35 g of the off-white amorphous intermediate; 46% yield; the intermediate was dissolved in trifluoroacetic acid (10 ml) and was stirred at ambient temperature for 16 hours. The mixture was vacuum filtered to collect the precipitate, which was recrystallized from methanol-chloroform to afford 0.055 g of the tan powder product; 26% yield from intermediate; mp 230–236° C. DEC; $^1$H-NMR (400 MHz; DMSO) δ11.73 (s, 1H), 9.46 (s, 1H), 9.38 (s, 1H), 7.80–7.75 (m, 2H), 7.79 (s, 2H), 7.50 (d, 1H, J=8.5 Hz), 6.82–6.78 (m, 1H); $^{19}$F-NMR (376 MHz; DMSO) δ−130.83 (s), −139.24 (s); MS (APCI+) 504 (M+1, 53), 488 (90), 471 (100); (APCI−) 502 (M−1, 12), 486 (100); IR (KBr) 3295, 1652, 1636, 1519, 1477, 1315, 1157 cm$^{-1}$; Anal. calcd/found for: C$_{13}$H$_9$ClF$_2$IN$_3$O$_4$S 0.41 CHCl$_3$ C, 29.15/29.05; H, 1.72/1.66; N, 7.60/7.21.

Example 4

Preparation of 2-(2-chloro-4-iodo-phenylamino)-3,4-difluoro-5-sulfamoyl-benzoic acid (PD 215730)

Solid 5-bis-(4-methoxybenzyl)sulfamoyl-2-(2-chloro-4-iodophenylamino)-3,4-difluorobenzoic acid (0.0995 g, 1.36×10$^{-4}$ mol) was dissolved in trifluoroacetic acid (5 ml) under a nitrogen atmosphere. The reaction mixture was stirred at ambient temperature for 65 hours. The mixture was vacuum filtered to isolate 55.2 mg of a fine white precipitate. The crude product was recrystallized from chloroform to afford 31.8 mg of the fluffy white solid product; 48% yield; mp 295–296° C. DEC; $^1$H-NMR (400 MHz; DMSO) δ9.77 (s, 1H), 8.16 (d, 1H, J=7.3 Hz), 7.82 (s, 3H), 7.56 (d, 1H, J=8.5 Hz), 6.97–6.92 (m, 1H); $^{19}$F-NMR (376 MHz; DMSO) δ−128.47 (s), −141.13 (d, 19.8 Hz); MS (APCI+) 489 (M+1, 5), 102 (100); (APCI−) 491 (32), 490 (18), 489 (100), 488 (18), 487 (M−1, 75); IR (KBr) 3372, 3244, 1688 cm$^{-1}$; Anal. calcd/found for: C$_{13}$H$_8$ClF$_2$IN$_2$O$_4$S C, 31.96/32.19; H, 1.65/1.81; N, 5.73/5.37.

Example 5

Preparation of 2-(2-chloro-4-iodo-phenylamino)-N-cyclopropylmethoxy-3,4-difluoro-5-dimethylsulfamoyl-benzamide (PD 250253)

Step a: Preparation of 2-(2-chloro-4-iodo-phenylamino)-3,4-difluoro-5-dimethylsulfamoyl-benzoic acid (PD 224339)

To a stirring solution comprised of 5-dimethylsulfamoyl-2,3,4-trifluorobenzoic acid (1.00 g, 3.53×10$^{-3}$ mol) in tetrahydrofuran (15 ml) at −78° C. under a nitrogen atmosphere was added a 1.0 M solution of lithium bis(trimethylsilyl) amide in tetrahydrofuran (Aldrich, 3.6 ml, 3.6×10$^{-3}$ mol). A lithium 2-chloro-4-iodoanilide suspension formed by adding a 1.0 M solution of lithium bis(trimethylsilyl)amide solution (7.2 ml, 7.2×10$^{-3}$ mol) to a solution comprised of 2-chloro-4-iodoaniline (0.94 g, 3.63×10$^{-3}$ mol) in tetrahydrofuran (15 ml) at −78° C. was added via canula to the lithium 5-dimethylsulfamoyl-2,3,4-trifluorobenzoate suspension. The cold bath was removed and the reaction mixture was stirred for one hour. The mixture was concentrated in vacuo to a crude solid. The crude product was suspended in diethyl ether (200 ml), to which suspension hydrogen chloride gas was introduced to produce a white precipitate. The precipitate was removed by vacuum filtration. The filtrate was concentrated in vacuo to give a dull-colored solid, which was triturated with hexanes-dichloromethane to afford 1.31 g of the white powder product; 72% yield; mp 218–222° C.; $^1$H-NMR (400 MHz; DMSO) δ9.89 (s, 1H), 8.06 (d, 1H, J=6.1 Hz), 7.85 (d, 1H, J=1.9 Hz), 7.58 (dd, 1H, J=8.5, 1.9 Hz), 7.03 (dd, 1H, J=8.3, 6.6 Hz), 2.71 (s, 6H); $^{19}$F-NMR (376 MHz; DMSO) δ−125.58 (d, J=18.3 Hz), −140.14 (d, J=16.8 Hz); MS (APCI+) 519 (40), 518 (15), 517 (M+1, 100); (APCI−) 517 (6), 516 (2), 515 (M−1, 5), 480 (45), 127 (100); IR (KBr) 3346, 1665, 1487, 1283 cm$^{-1}$; Anal. calcd/found for: $C_{15}H_{12}ClF_2IN_2O_4S$ C, 34.87/34.98; H, 2.34/2.32; N, 5.42/5.32.

Step b: Preparation of 2-(2-chloro-4-iodo-phenylamino)-N-cyclopropylmethoxy-3,4-difluoro-5-dimethylsulfamoyl-benzamide To a suspension comprised of 2-(2-chloro-4-iodo-phenylamino)-3,4-difluoro-5-dimethylsulfamoyl-benzoic acid (0.5 g, 9.68×10$^{-4}$ mol) and cyclopropylmethoxylamine hydrochloride (0.13 g, 1.05×10$^{-3}$ mol) in a 1:1 v/v mixture of dichloromethane-tetrahydrofuran (10 ml) was added diisopropylethylamine (0.65 ml, 3.73×10$^{-3}$ mol) followed by the addition of solid PyBOP (0.55 g, 1.06×10$^{-3}$ mol). The reaction mixture was stirred at ambient temperature for three days. The mixture was concentrated in vacuo to a red oil. The crude product was treated with 10% aqueous hydrochloric acid (150 ml) and was extracted with diethyl ether (150 ml). The organic phase was dried (MgSO$_4$) and concentrated in vacuo to a crude solid. The solid was triturated with dichloromethane-hexanes and recovered by vacuum filtration to afford 0.3558 g of the white powder product; 63% yield; mp 222–225° C. DEC; $^1$H-NMR (400 MHz; DMSO) δ11.97 (s, 1H), 9.32 (s, 1H), 7.60 (d, 1H, J=1.9 Hz), 7.49 (d, 1H, J=5.8 Hz), 7.33 (dd, 1H, J=8.4, 1.9 Hz), 6.70 (dd, 1H, 8.4, 6.3 Hz), 3.43 (d, 2H, J=7.2 Hz), 2.53 (s, 6H), 0.87–0.83 (m, 1H), 0.30–0.25 (m, 2H), 0.03–0.00 (m, 2H); $^{19}$F-NMR (376 MHz; DMSO) δ−127.67 (d, J=19.8 Hz), −139.32 (d, J=19.8 Hz); MS (APCI+) 586 (M+1, 100); (APCI−) 584 (M−1, 40), 514 (100); IR (KBr) 3263, 1644, 1585, 1507, 1480 cm$^{-1}$; Anal. calcd/found for: $C_{19}H_{19}ClF_2IN_3O_4S$ C, 38.96/39.08; H, 3.27/3.18; N, 7.17/7.17.

Example 6

Preparation of N-cyclopropylmethoxy-3,4-difluoro-5-dimethylsulfamoyl-2-(4-iodo-2-methyl-phenylamino)-benzamide (PD 252745)

Step a: Preparation of 3,4-difluoro-5-dimethylsulfamoyl-2-(4-iodo-2-methyl-phenylamino)-benzoic acid (PD 224340)

Same procedure and same scale as Example 4, Step a, except 4-iodo-2-methylaniline was used instead of 2-chloro-4-iodoaniline; afforded 0.9592 g of the off-white powder product; 55% yield; mp 235–238° C.; $^1$H-NMR (400 MHz;

DMSO) δ9.69 (s, 1H), 8.04 (d, 1H, J=6.1 Hz), 7.60 (d, 1H, J=1.5 Hz), 7.45 (dd, 1H, J=8.3, 1.7 Hz), 6.88 (dd, 1H, J=8.3, 5.4 Hz), 2.70 (s, 6H), 2.21 (s, 3H); $^{19}$F-NMR (376 MHz; DMSO) δ−126.25 (d, J=16.8 Hz), −142.74 (d, J=19.8 Hz); MS (APCI+) 497 (M+1, 69), 357 (70), 316 (100); (APCI−) 495 (M−1, 3), 127 (100); IR (KBr) 3240, 1686, 1512, 1473, 1341, 1151 cm$^{-1}$; Anal. calcd/found for: $C_{16}H_{15}F_2IN_2O_4S$ C, 38.72/38.70; H, 3.05/3.01; N, 5.64/5.49.

Step b: Preparation of N-cyclopropylmethoxy-3,4-difluoro-5-dimethylsulfamoyl-2-(4-iodo-2-methyl-phenylamino)-benzamide Same procedure and same scale as Example 4, Step b, except the product was purified by recrystallization from absolute ethanol to afford 0.1718 g of the pale yellow microcrystalline product; 28% yield; mp 171–172° C.; $^1$H-NMR (400 MHz; DMSO) δ11.79 (s, 1H), 8.91 (s, 1H), 7.40 (d, 1H, J=4.3 Hz), 7.36 (s, 1H), 7.21 (d, 1H, J=8.2 Hz), 6.54 (dd, 1H, 8.2, 4.3 Hz), 3.30 (d, 2H, J=6.5 Hz), 2.52 (s, 6H), 2.00 (s, 3H), 0.85–0.75 (m, 1H), 0.29 (d, 2H, J=7.7 Hz), 0.01 (d, 2H, J=4.1 Hz); $^{19}$F-NMR (376 MHz; DMSO) δ−128.94 (s), −143.32 (d, J=19.8 Hz); MS (APCI+) 566 (M+1, 100); (APCI−) 564 (M−1, 85), 494 (100); IR (KBr) 1649, 1609, 1588, 1512, 1475 cm$^{-1}$; Anal. calcd/found for: $C_{20}H_{22}F_2IN_3O_4S$ C, 42.49/42.42; H, 3.92/3.78; N, 7.43/7.40.

Example 7

Preparation of 2-(2-chloro-4-iodo-phenylamino)-N-hydroxy-4-dimethylsulfamoyl-benzamide Step a: Preparation of 4-methyl-benzene-N,N-dimethylsulfonamide To a stirring solution comprised of para-toluenesulfonyl chloride in dichloromethane at 0° C. is introduced excess gaseous dimethylamine. The precipitate is removed by filtration and the filtrate is concentrated in vacuo to obtain the product.

Step b: Preparation of 4-methyl-3-nitro-benzene-N,N-dimethylsulfonamide

To a gently stirring solution comprised of 1 molar equivalent of fuming nitric acid in excess concentrated sulfuric acid is added 1 molar equivalent of 4-methyl-benzene-N,N-dimethylsulfonamide in increments. The mixture is stirred for one hour and then poured over chilled water. The mixture is extracted with a suitable solvent like diethyl ether or dichloromethane. The organic phase is dried over a suitable drying agent like magnesium sulfate and concentrated in vacuo to afford a crude product which may be purified by normal methods such as chromatography or crystallization from a solvent like chloroform or heptane.

Step c: Preparation of 3-amino-4-methyl-benzene-N,N-dimethylsulfonamide

The compound 4-methyl-3-nitro-benzene-N,N-dimethylsulfonamide is dissolved in ethanol. A catalyst like Raney nickel is added and the mixture hydrogenated in a shaker. The catalyst is removed by filtration. The solvent is removed in vacuo to give a product which may be purified if necessary by chromatography or crystallization from an appropriate solvent like chloroform or heptane-ethyl acetate.

Step d: Preparation of 3-fluoro-4-methyl-benzene-N,N-dimethylsulfonamide

The compound 3-amino-4-methyl-benzene-N,N-dimethylsulfonamide is diazotized with an alkyl nitrite like tert-butyl nitrite under anhydrous conditions in a non-reactive solvent like tetrahydrofuran or dichloromethane. The intermediate diazonium species is then treated with pyridinium fluoride to give the product, which may be purified by chromatography or crystallization.

Step e: Preparation of 4-dimethylsulfamoyl-2-fluoro-benzoic acid

A mixture comprised of 3-fluoro-4-methyl-benzene-N,N-dimethylsulfonamide and potassium permanganate (2.2 molar equivalents) in water is brought to reflux for four hours. The reaction mixture is filtered through celite. The filtrate is treated with activated carbon and refiltered through fresh celite. The second filtrate is acidified with concentrated hydrochloric acid to pH 0. The mixture is allowed to cool and is extracted with diethyl ether. The organic phase is dried over a drying agent like magnesium sulfate and is concentrated in vacuo. The product may be purified by recrystallization from an appropriate solvent like ethanol or chloroform.

Step f: Preparation of 2-(2-chloro-4-iodo-phenylamino)-4-dimethylsulfamoyl-benzoic acid To a stirring cold (−78° C.) solution comprised of 2-chloro-4-iodoaniline (1 molar equivalent) in anhydrous tetrahydrofuran under a nitrogen atmosphere is added a commercially available lithium diisopropylamide solution (Aldrich, 2.0 M in tetrahydrofuran/heptane/ethylbenzene, 1 molar equivalent). After stirring for 5 minutes, a solution comprised of 4-dimethylsulfamoyl-2-fluoro-benzoic acid (1 molar equivalent) in tetrahydrofuran is added. The cold bath is removed and the reaction mixture is stirred for 2 hours. The reaction mixture is then partitioned between diethyl ether and dilute aqueous hydrochloric acid. The organic phase is washed with brine, dried over magnesium sulfate, and concentrated in vacuo to afford a product which may be purified by chromatography of recrystallization from an appropriate solvent like chloroform or heptane-ethanol.

Step g: Preparation of 2-(2-chloro-4-iodo-phenylamino)-4-dimethylsulfamoyl-benzoic acid O-(tetrahydro-2H-pyran-2-yl)-oxyamide A solution comprised of 2-(2-chloro-4-iodo-phenylamino)-4-dimethylsulfamoyl-benzoic acid, O-(tetrahydro-2H-pyran-2-yl)-hydroxylamine (1.25 molar equivalents), benzotriazole-1-yl-oxy-tris-pyrrolidino-phosphonium hexafluorophosphate (1.25 molar equivalents), and diisopropylethylamine (3 molar equivalents) in 1:1 v/v tetrahydrofuran-dichloromethane is stirred for 30 minutes. The reaction mixture is concentrated in vacuo and the residue is purified by flash chromatography; elution with dichloromethane affords the desired product. The product may be recrystallized with an appropriate solvent like methanol if further purification is necessary.

Step h: Preparation of 2-(2-chloro-4-iodo-phenylamino)-4-dimethylsulfamoyl-N-hydroxy-benzamide The compound 2-(2-chloro-4-iodo-phenylamino)-4-dimethylsulfamoyl-benzoic acid O-(tetrahydro-2H-pyran-2-yl)-oxyamide is dissolved in an appropriate hydrogen chloride-saturated solvent like methanol or ethanol. Once homogeneous, the solution is concentrated in vacuo to give the desired product. The product may be triturated with an appropriate solvent like chloroform or dichloromethane if further purification is necessary.

Example 8
Cascade Assay for Inhibitors of the MAP Kinase Pathway

Incorporation of $^{32}P$ into myelin basic protein (MBP) is assayed in the presence of a glutathione S-transferase fusion protein containing p44MAP kinase (GST-MAPK) and a glutathione S-transferase fusion protein containing p45MEK (GST-MEK). The assay solution contains 20 mM HEPES, pH 7.4, 10 mM $MgCl_2$, 1 mM $MnCl_2$, 1 mM EGTA, 50 μM [γ-$^{32}P$]ATP, 10 μg GST-MEK, 0.5 μg GST-MAPK and 40 μg MBP in a final volume of 100 μL. Reactions are stopped after 20 minutes by addition of trichloroacetic acid and filtered through a GF/C filter mat. $^{32}P$ retained on the filter mat is determined using a 120S Betaplate. Compounds are assessed at 10 μM for ability to inhibit incorporation of $^{32}P$.

To ascertain whether compounds are inhibiting GST-MEK or GST MAPK, two additional protocols are employed. In the first protocol, compounds are added to tubes containing GST-MEK, followed by addition of GST-MAPK, MBP and [β-$^{32}P$]ATP. In the second protocol, compounds are added to tubes containing both GST-MEK and GST-MAPK, followed by MBP and [β-$^{32}P$]ATP.

Compounds that show activity in both protocols are scored as MAPK inhibitors, while compounds showing activity in only the first protocol are scored as MEK inhibitors.

Example 9
In Vitro MAP Kinase Assay

Inhibitory activity can be confirmed in direct assays. For MAP kinase, 1 μg GST-MAPK is incubated with 40 μg MBP for 15 minutes at 30° C. in a final volume of 50 μL containing 50 mM Tris (pH 7.5), 10 μM $MgCl_2$, 2 μM EGTA, and 10 μM [γ-$^{32}P$]ATP. The reaction is stopped by addition of Laemmli SDS sample buffer and phosphorylated MBP resolved by electrophoresis on a 10% polyacrylamide gel. Radioactivity incorporated into MBP is determined by both autoradiography, and scintillation counting of excised bands.

Example 10
In Vitro MEK Assay

For evaluation of direct MEK activity, 10 μg GST-MEK, is incubated with 5 μg of a glutathione S-transferase fusion protein containing p44MAP kinase with a lysine to alanine mutation at position 71 (GST-MAPK-KA). This mutation eliminates kinase activity of MAPK, so only kinase activity attributed to the added MEK remains. Incubations are 15 minutes at 30° C. in a final volume of 50 μL containing 50 mM Tris (pH 7.5), 10 μM $MgCl_2$, 2, μM EGTA, and 10 μM [γ-$^{32}P$]ATP. The reaction is stopped by addition of Laemrnli SDS sample buffer. Phosphorylated GST-MAPK-KA is resolved by electrophoresis on a 10% polyacrylamide gel. Radioactivity incorporated into GST-MAPK-KA is determined by autoradiography, and subsequent scintillation counting of excised bands. Additionally, an artificially activated MEK containing serine to glutamate mutations at positions 218 and 222 (GST-MEK-2E) is used. When these two sites are phosphorylated, MEK activity is increased. Phosphorylation of these sites can be mimicked by mutation of the serine residues to glutamate. For this assay, 5 μg GST-MEK-2E is incubated with 5 μg GST-MAPK-KA for 15 minutes at 30° C. in the same reaction buffer as described above. Reactions are terminated and analyzed as above.

Example 11
Whole Cell MAP Kinase Assay

To determine if compounds block activation of MAP kinase in whole cells, the following protocol is used. Cells are plated in multi-well plates and grown to confluence. Cells are serum-deprived overnight. Cells are exposed to the desired concentrations of compound or vehicle (DMSO) for 30 minutes, followed by addition of a growth factor, for example, PDGF (100 ng/mL). After a 5-minute treatment with the growth factor, cells are washed with PBS, and lysed in a buffer consisting of 70 mM NaCl, 10 mM HEPES (pH 7.4), 50 mM glycerol phosphate, and 1% Triton X-100. Lysates are clarified by centrifugation at 13,000×g for 10 minutes. Five micrograms of the resulting supernatants are incubated with 10 μg microtubule associated protein-2

(Map2) for 15 minutes at 30° C. in a final volume of 25 µL containing 50 mM Tris (pH 7.4), 10 mM $MgCl_2$, 2 mM EGTA and 30 µM [γ-$^{32}$P]ATP. Reactions are terminated by addition of Laermmli sample buffer. Phosphorylated Map2 is resolved on 7.5% acrylamide gels and incorporated radioactivity is determined by scintillation counting of excised bands.

Example 12
Monolayer Growth

Cells are plated into multi-well plates at 10 to 20,000 cells/mL. Forty-eight hours after seeding, test compounds are added to the cell growth medium and incubation is continued for 2 additional days. Cells are then removed from the wells by incubation with trypsin and enumerated with a Coulter counter.

Example 13
Growth in Soft-agar

Cells are seeded into 35-mm dishes at 5 to 10,000 cells/dish using growth medium containing 0.3% agar. After chilling to solidify the agar, cells are transferred to a 37° C. incubator. After 7 to 10 days' growth. visible colonies are manually enumerated with the aid of a dissecting microscope.

Example 14
Collagen-Induced Arthritis in Mice

Type II collagen-induced arthritis (CIA) in mice is an experimental model of arthritis that has a number of pathologic, immunologic, and genetic features in common with rheumatoid arthritis. The disease is induced by immunization of DBA/1 mice with 100 µg type II collagen, which is a major component of joint cartilage, delivered intradermally in Freund's complete adjuvant. The disease susceptibility is regulated by the class II MHC gene locus, which is analogous to the association of rheumatoid arthritis with HLA-DR4.

A progressive and inflammatory arthritis develops in the majority of mice immunized, characterized by paw width increases of up to 100%. A test compound is administered to mice in a range of amounts, such as 20, 60, 100, and 200 mg/kg body weight/day. The duration of the test can be several weeks to a few months, such as 40, 60, or 80 days. A clinical scoring index is used to assess disease progression from erythema and edema (stage 1), joint distortion (stage 2), to joint ankylosis (stage 3). The disease is variable in that it can affect one or all paws in an animal, resulting in a total possible score of 12 for each mouse. Histopathology of an arthritic joint reveals synovitis, pannus formation, and cartilage and bone erosions. All mouse strains that are susceptible to CIA are high antibody responders to type II collagen, and there is a marked cellular response to CII.

Example 15
SCW-induced Monoarticular Arthritis

Arthritis is induced as described by Schwab, et al., *Infection and Immunity*, 59:4436–4442 (1991) with minor modifications. Rats receive 6 µg sonicated SCW [in 10 µl Dulbecco's PBS (DPBS)] by an intraarticular injection into the right tibiotalar joint on day 0. On day 21, the DTH is initiated with 100 µg of SCW (250 µl) administered i.v. For oral compound studies, compounds are suspended in vehicle (0.5% hydroxypropyl-methylcellulose/0.2% Tween 80), sonicated, and administered twice daily (10 ml/kg volume) beginning 1 hr prior to reactivation with SCW. Compounds are administered in amounts between 10 and 500 mg/kg body weight/day, such as 20, 30, 60, 100, 200, and 300 mg/kg/day. Edema measurements are obtained by determining the baseline volumes of the sensitized hindpaw before reactivation on day 21, and comparing them with volumes at subsequent time points such as day 22, 23, 24, and 25. Paw volume is determined by mercury plethysmography.

Example 16
Mouse Ear-heart Transplant Model

Fey, T. A. et al. describe methods for transplanting split-heart neonatal cardiac grafts into the ear pinna of mice and rats (*J. Pharm. and Toxic. Meth.* 39:9–17 (1998)). Compounds are dissolved in solutions containing combinations of absolute ethanol, 0.2% hydroxypropyl methylcellulose in water, propylene glycol, cremophor, and dextrose, or other solvent or suspending vehicle. Mice are dosed orally or intraperitoneally once, twice or three times daily from the day of transplant (day 0) through day 13 or until grafts have been rejected. Rats are dosed once, twice, or three times daily from day 0 through day 13. Each animal is anesthetized and an incision is made at the base of the recipient ear, cutting only the dorsal epidermis and dermis. The incision is spread open and down to the cartilage parallel to the head, and sufficiently wide to accommodate the appropriate tunneling for a rat or insertion tool for a mouse. A neonatal mouse or rat pup less than 60 hours old is anesthetized and cervically dislocated. The heart is removed from the chest, rinsed with saline, bisected longitudinally with a scalpel, and rinsed with sterile saline. The donor heart fragment is placed into the preformed tunnel with the insertion tool and air or residual fluid is gently expressed from the tunnel with light pressure. No suturing, adhesive bonding, bandaging, or treatment with antibiotics is required.

Implants are examined at 10–20-fold magnification with a stereoscopic dissecting microscope without anesthesia. Recipients whose grafts are not visibly beating may be anesthetized and evaluated for the presence of electrical activity using Grass E-2 platinum subdermal pin microelectodes placed either in the pinna or directly into the graft and a tachograph. Implants can be examined 1–4 times a day for 10, 20, 30 or more days. The ability of a test compound to ameliorate symptoms of transplant rejection can be compared with a control compound such as cyclosporine, tacrolimus, or orally-administered lefluonomide.

Example 17
Murine Ovalbumin-induced Eosinophilia

Female C57BL/6 mice are obtained from the Jackson Laboratory (Bar Harbor, Me.). All animals are given food and water ad libitum. Mice are sensitized with a single i.p. injection of OVA (grade V, Sigma Chemical Company, St. Louis, Mo.) adsorbed to alum, (10 µg OVA+9 mg alum in 200 µl saline) or vehicle control, (9 mg alum in 200 µl saline) on day 0. On day 14, the mice are challenged with a 12-minute inhalation of an aerosol consisting of 1.5% OVA (weight/volume) in saline produced by a nebulizer (small particle generator, model SPAG-2; ICN Pharmaceuticals, Costa Mesa, Calif.). Groups of eight mice are dosed with oral vehicle (0.5% hydroxypropylmethylcellulose/0.25% TWEEN-80), or a test compound at 10, 30, or 100 mg/kg in oral vehicle, 200 µl per mouse p.o. Dosing is performed once per day starting on day 7 or day 13, and extending through day 16.

For determination of pulmonary eosinophilia, three days after the first OVA aerosol challenge (day 17), the mice are anesthetized with an i.p. injection of anesthetic (Ketamine/Acepromazine/Xylazine), and the tracheae is exposed and cannulated. The lungs and upper airways are lavaged twice with 0.5 ml of cold PBS. A portion (200 µl) of the bronchoalveolar lavage (BAL) fluid is enumerated using a Coulter counter Model ZB1 (Coulter Electronics, Hialeah, Fla.). The remaining BAL fluid is then centrifuged at 300× g for five minutes, and the cells are resuspended in 1 ml of HBSS (Gibco BRL) containing 0.5% fetal calf serum (HyClone) and 10 mM HEPES (Gibco BRL). The cell suspension is centrifuged in a cytospin (Shandon Southern Instruments, Sewickley, Pa.) and stained by Diff Quick (American Scientific Products, McGraw Park, Ill.) to differentiate BAL leukocytes into neutrophil, eosinophil, monocyte or lymphocyte subsets. The number of eosinophils in the BAL fluid is determined by multiplying the percentage of eosinophils by the total cell count.

Example 18

Caco-2 Cell Studies

Cell transport studies were conducted with Caco-2 cells grown on Snapwells between 22 to 28 days postseeding. Typically, 10 mM MES buffer (pH 6.5) with 5 mM KCl, 135 mM NaCl and 1.8 mM $CaCl_2$ was used for the apical side and 10 mM MOPS (pH 7.4) with 5 mM KCl, 132.5 mM NaCl and 1.8 mM $CaCl_2$ with 5 mM D-Glucose was used for the basolateral side. After washing the monolayers, appropriate buffers were pipetted into the respective chambers and the cells were pre-equilibrated at 37° C. for at least 15 min. On the day of the experiment the growth media was aspirated and the cell monolayers were preequilibrated with appropriate buffers at 37° C. for at least 15 min. Thereafter, TEER measurements were performed to confirm the integrity of the monolayers. Transepithelial flux measurements were made by mounting the cell monolayers in a side-by-side diffusion chamber system (Precision Instrument Design, Tahoe City, Calif.). Temperature was maintained at 37° C. with a circulating water jacket. The solutions were mixed with gas-lift circulation with 95% oxygen-5% carbon dioxide. Donor solutions with PD compounds, [$^{14}$C] mannitol (leakage marker) and [$^3$H] metoprolol (reference compound) were added to the apical chamber. Donor and receiver samples were collected at selected time intervals for up to 3 hours. Radiolabelled mannitol and metoprolol were analyzed using scintillation counting (TopCount, Packard Instruments, Downers Grove, Ill.). PD compounds were analyzed using a LC/MS/MS method. Apparent permeability coefficients were calculated using the following equation.

$$P_{app}=(V*dC)/(A.C_o.dt)$$

where V=volume of the receiver solution in ml, A=surface area in $cm^2$, $C_o$=initial donor concentration in mM and dC/dt=change in the drug concentration in the receiver chamber over time.

Example 19

Metabolic Stability in Human and Rat Liver Microsomes

Compounds are individually incubated (5 μM, dissolved in DMSO) with human and rat liver microsomes (0.5 mg/mL protein) in 50 mM KHPO4 buffer at 37° C. in the presence of 1.0 mM NADPH. At 0, 10, 20 and 40 minutes, 100 μL aliquots are removed and added to 300 μL of acetonitrile. Standard curves are run in a similar manner with each compound at concentrations: 7.5 μM, 3.75 μM, 2.5 μM, 1.25 μM. The samples are analyzed for parent concentration by LC/MS/MS. The in vitro metabolic half-life determinations are determined from the concentration vs. time plots using WinNonlin. These in vitro data represent the rate of oxidative and hydrolytic metabolism.

Example 20

Below is a table of selected compounds.

| Compound | Mean $IC_{50}$ | Individual $IC_{50}$s |
|---|---|---|
| PD 0298458 | 0.48 | 0.56, 0.41 |
| PD 0298459 | 0.24 | 0.16, 0.32 |
| PD 0298460 | 0.68 | 0.54, 0.83 |
| PD 0298463 | 5.6 | n = 1 |
| PD 0298464 | 2.6 | 2.9, 2.4 |
| PD 0298465 | 1.04 | 1.2, 0.89 |
| PD 0298467 | 0.92 | 1.4, 0.44 |

5979 STRUCTURE CHART

| PD Number | APK $IC_{50}$ (nM) | C26 Cells (nM) | Structure |
|---|---|---|---|
| 193846 | 222 | | 2-(2-Chloro-4-iodo-phenlylamino)-5-dimethylsulfamoyl-3,4-difluoro-benzoic acid methyl ester |
| 215729 | 3000 | | 5-[Bis-(4-methoxy-benzyl)-sulfamoyl]-2-(2-chloro-4-iodo-phenylamino)-3,4-difluoro-benzoic acid |
| 215730 | 781 | | 2-(2-Chloro-4-iodo-phenylamino)-3,4-difluoro-5-sulfamoyl-benzoic acid |
| 218774 | >3000 | | 5-[Bis-(4-methoxy-benzyl)-sulfamoyl]-2-(2-chloro-4-iodo-phenylamino)-N-cyclopropylmethoxy-3,4-difluoro-benzamide |
| 219622 | 186 | 1600 | 2-(2-Chloro-4-iodo-phenylamino)-N-cyclopropylmethoxy-3,4-difluoro-5-sulfamoyl-benzamide |
| 219795 | >3000 | | 2-(2-Chloro-4-iodo-phenylamino)-3,4-difluoro-5-(methyl-pyridin-3-ylmethyl-sulfamoyl)-benzoic acid |
| 224213 | 122 | 9100 | 2-(2-Chloro-4-iodo-phenylamino)-3,4-difluoro-N-hydroxy-5-sulfamoyl-benzamide |
| 224339 | 283.5 | >10,000 | 2-(2-Chloro-4-iodo-phenylamino)-5-dimethylsulfamoyl-3,4-difluoro-benzoic acid |
| 224340 | 440.5 | >10,000 | 5-Dimethylsulfamoyl-3,4-difluoro-2-(4-iodo-2-methyl-phenylamino)-benzoic acid |
| 250253 | 936.5 | | 2-(2-Chloro-4-iodo-phenylamino)-N-cyclopropylmethoxy-5-dimethylsulfamoyl-3,4-difluoro-benzamide |
| 252745 | 3700 | | N-Cyclopropylmethoxy-5-dimethylsulfamoyl-3,4-difluoro-2-(4-iodo-2-methyl-phenylamino)-benzamide |

F. Other Embodiments

From the above disclosure and examples, and from the claims below, the essential features of the invention are readily apparent. The scope of the invention also encompasses various modifications and adaptations within the knowledge of a person of ordinary skill. Examples include a disclosed compound modified by addition or removal of a protecting group, or an ester, pharmaceutical salt, hydrate, acid, or amide of a disclosed compound. Publications cited herein are hereby incorporated by reference in their entirety.

What is claimed is:

1. A method for treating brain cancer, breast cancer, lung cancer, ovarian cancer, pancreatic cancer, prostate cancer, renal cancer, or colorectal cancer, said method comprising administering to a patient in need of such treatment a pharmaceutically-effective amount of a compound of formula (I):

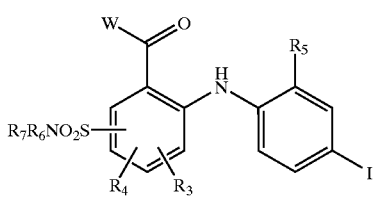

(I)

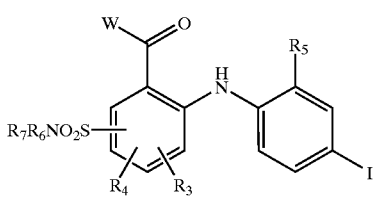

(I)

wherein
- W is $OR_1$, $NR_2OR_1$, $NR_AR_B$, $NR_2NR_AR_B$, or $NR_2(CH_2)_{2-4}NR_AR_B$;
- $R_1$ is H, $C_{1-8}$ alkyl, $C_{3-8}$ alkenyl, $C_{3-8}$ alkynyl, $C_{3-8}$ cycloalkyl, phenyl, (phenyl)$C_{1-4}$ alkyl, (phenyl)$C_{3-4}$ alkenyl, (phenyl)$C_{3-4}$ alkynyl, ($C_{3-8}$ cycloalkyl)-$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, ($C_{3-8}$ heterocyclic radical)$C_{3-4}$ alkenyl, ($C_{3-8}$ heterocyclic radical)$C_{3-4}$ alkynyl or $(CH_2)_{2-4}NR_AR_B$;
- $R_2$ is H, phenyl, $C_{1-4}$ alkyl, $C_{3-4}$ alkenyl, $C_{3-8}$ alkynyl, $C_{3-8}$ cycloalkyl, or ($C_{3-8}$ cycloalkyl)$C_{1-4}$ alkyl;
- $R_A$ is H, $C_{3-8}$ alkyl, $C_{3-8}$ alkenyl, $C_{3-8}$ alkynyl, $C_{3-8}$ cycloalkyl, phenyl, ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ heterocyclic radical)$C_{1-4}$ alkyl, (aminosulfonyl)phenyl, [(aminosulfonyl)phenyl]$C_{1-4}$ alkyl, (aminosulfonyl)$C_{1-6}$ alkyl, (aminosulfonyl)$C_{3-6}$ (aminosulfonyl)$C_{3-4}$ cycloalkyl, or [(aminosulfonyl)$C_{3-6}$ cycloalkyl]$C_1$ alkyl;
- $R_B$ is H, $C_{1-8}$ alkyl, $C_{3-8}$ alkenyl, $C_{3-8}$ alkynyl, $C_{3-8}$ cycloalkyl, or $C_{6-8}$ aryl;
- $R_3$ is H, F, Cl, Br, or $NO_2$;
- $R_4$ is H or F;
- $R_5$ is H, methyl or Cl;
- $R_6$ is H, $C_{1-4}$ alkyl, hydroxyopyl, $(CH_2)_{2-4}(NR_CR_D)$, phenyl, 2-pyridyl, 3-pyridyl, 4-pyridyl or $CH_2Ar$, where Ar is phenyl, 2-pyridyl, 3-pyridyl, or 4-pyridyl;
- $R_7$ is H, $C_{1-4}$ alkyl, hydroxyethyl, hydroxypropyl, $(CH_2)_{2-4}(NR_CR_D)$, phenyl, 2-pyridyl, 3-pridyl, 4-pyridyl, or $CH_2Ar'$, where Ar' is phenyl, 2-pyridyl, 3-pyridyl, or 4-pyridyl;
- each of $R_C$ and $R_D$ is independently selected from H, $C_{1-6}$ alkyl, $C_{3-4}$ alkenyl, $C_{3-4}$ alkynyl, $C_{1-6}$ cycloalkyl, $C_{3-6}$ heterocyclic radical, and phenyl; $NR_CR_D$ is also selected from the group consisting of morpholinyl, piperazinyl, pyrrolidinyl, and piperadinyl;
- wherein each hydrocarbon radical or heterocyclic radical above is optionally substituted with between 1 and 3 substituents independently selected from halo, $C_{1-4}$ alkyl, $C_{3-6}$ cycloalkyl, $C_{2-4}$ alkenyl, $C_{2-4}$ alkynyl, phenyl, hydroxy, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$ alkyl, hydroxy, amino, and $NO_2$;
- or a phannaceutically-acceptable salt or $C_{1-6}$ ester thereof.

2. A method for treating a viral infection, selected from the group consisting of HIV, hepatitis B virus, human papilloma virus, cytomegalovirus, and Epstein Barr virus, said method comprising administering to a patient in need of such treatment a pharmaceutically-effective amount of a compound of formula (I):

wherein
- W is $OR_1$, $NR_2OR_1$, $NR_AR_B$, $NR_2NR_AR_B$, or $NR_2(CH_2)_{2-4}NR_AR_B$;
- $R_1$ is H, $C_{1-8}$ alkyl, $C_{3-8}$ alkenyl, $C_{3-8}$ alkynyl, $C_{3-8}$ cycloalkyl, phenyl, (phenyl)$C_{1-4}$ alkyl, (phenyl)$C_{3-4}$ alkenyl, phenyl)$C_{3-4}$ alkynyl, ($C_{3-8}$ cycloalkyl)-$C_{1-4}$ alkyl, ($C_{3-8}$ cycloalkyl)$C_{3-4}$ alkenyl, ($C_{3-8}$ acycloalkyl)$C_{3-4}$ alkynyl, $C_{3-8}$ heterocyclic radical, ($C_{3-8}$ heterocyclic radical)$C_{1-4}$ alkyl, ($C_{3-8}$ heterocyclic radical)$C_{3-4}$ alkenyl, ($C_{3-8}$ heterocyclic radical)$C_{3-4}$ alkynyl or $(CH_2)_{2-4}NR_AR_B$;
- $R_2$ is H, phenyl, $C_{1-4}$ alkyl, $C_{3-4}$ alkenyl, $C_{3-8}$ alkynyl, $C_{3-8}$ cycloalkyl, or ($C_{3-8}$ cycloalkyl)-$C_{1-4}$ alkyl;
- $R_A$ is H, $C_{3-8}$ alkyl, $C_{3-8}$ alkenyl, $C_{3-8}$ cycloakyl, phenyl ($C_{3-8}$ cycloalkyl)$C_{1-4}$ alkyl, ($C_{3-8}$ cycloalkyl)$C_{3-4}$ alkenyl, ($C_{3-8}$ cycloalkyl)$C_{3-4}$ alkynyl, $C_{3-8}$ heterocyclic radical, ($C_{3-8}$ hererocyclic radical)$C_{1-4}$ alkyl, (aminosulfonyl)phenyl, [(aminosulfonyl)phenyl]$C_{1-4}$ alkyl, (aminosulfonyl)$C_{1-6}$ alkyl, (aminosulfonyl)$C_{3-6}$ cycloalkyl, or [(aminosulfonyl)$C_{3-6}$ cycloalkyl]$C_{1-4}$ alkyl;
- $R_B$ is H, $C_{1-8}$ alkyl, $C_{3-8}$ alkenyl, $C_{3-8}$ alkynyl, $C_{3-8}$ cycloalkyl, or $C_{6-8}$ aryl;
- $R_3$ is H, F, Cl, Br, or $NO_2$;
- $R_4$ is H or F,
- $R_5$ is H, methyl or Cl;
- $R_4$ is H, $C_{1-4}$ alkyl, hydroxyethyl, hydroxypropyl, $(CH_2)_{2-4}(NR_CR_D)$, phenyl, 2-pyridyl, 3-pyridyl, 4-pyridyl or $CH_2Ar$, where Ar is phenyl, 2-pyridyl, 3-pyridyl, or 4-pyridyl;
- $R_7$ is H, $C_{1-4}$ alkyl, hydroxyethyl, hydroxypropyl, $(CH_2)_{2-4}(NR_CR_D)$ phenyl, 2-pyridyl, 3-pyridyl, 4-pyridyl, or $CH_2Ar'$, where Ar' is phenyl, 2-pyridyl, 3-pyridyl, or 4-pyridyl;
- each of $R_C$ and $R_D$ independently selected from H, $C_{1-6}$ alkyl, $C_{3-4}$ alkenyl, $C_{3-4}$ alkynyl, $C_{3-6}$ cycloalkyl, $C_{3-6}$ heterocyclic radical, and phenyl; $NR_CR_D$ is also selected from the group consisting of morpholinyl, piperazinyl, pyrrolidinyl, and piperadinyl;
- wherein each hydrocarbon radical or heterocyclic radical above is optionally substituted with between 1 and 3 substituents independently selected from halo, $C_{1-4}$ alkyl, $C_{3-6}$ cycloalkyl, $C_{2-4}$ alkenyl, $C_{2-4}$ alkynyl, phenyl, hydroxy, amino, (amino)sulfonyl, and $NO_2$, wherein each substituent alkyl, cycloalkyl, alkenyl, alkynyl or phenyl is in turn optionally substituted with between 1 and 3 substituents independently selected from halo, $C_{1-2}$ alkyl, hydroxy, amino, and $NO_2$;
- or a pharmaceutically-acceptable salt or $C_{1-6}$ ester thereof.

3. A method of claim 2, wherein said viral infection is an infection of HIV.

* * * * *